(12) United States Patent
Feldman et al.

(10) Patent No.: US 11,229,382 B2
(45) Date of Patent: Jan. 25, 2022

(54) SELF-POWERED ANALYTE SENSOR AND DEVICES USING THE SAME

(71) Applicant: Abbott Diabetes Care Inc., Alameda, CA (US)

(72) Inventors: Benjamin Jay Feldman, Berkeley, CA (US); Lei He, Moraga, CA (US); Michael Love, Pleasanton, CA (US); Hyun Cho, Berkeley, CA (US)

(73) Assignee: Abbott Diabetes Care Inc., Alameda, CA (US)

(*) Notice: Subject to any disclaimer, the term of this patent is extended or adjusted under 35 U.S.C. 154(b) by 188 days.

(21) Appl. No.: 14/529,427

(22) Filed: Oct. 31, 2014

(65) Prior Publication Data

US 2015/0182153 A1 Jul. 2, 2015

Related U.S. Application Data

(60) Provisional application No. 61/922,404, filed on Dec. 31, 2013.

(51) Int. Cl.
*A61B 5/145* (2006.01)
*A61B 5/00* (2006.01)
*A61B 5/1486* (2006.01)

(52) U.S. Cl.
CPC ........ *A61B 5/14532* (2013.01); *A61B 5/0004* (2013.01); *A61B 5/1451* (2013.01); *A61B 5/14546* (2013.01); *A61B 5/6833* (2013.01); *A61B 5/7225* (2013.01); *A61B 5/7235* (2013.01); *A61B 5/1486* (2013.01); *A61B 2560/0204* (2013.01); *A61B 2560/029* (2013.01); *A61B 2560/0214* (2013.01)

(58) Field of Classification Search
CPC ............ A61B 5/14532; A61B 5/14865; A61B 5/14546; A61B 5/14503; A61B 5/1451
See application file for complete search history.

(56) References Cited

U.S. PATENT DOCUMENTS

| | | | |
|---|---|---|---|
| 3,164,534 | A | 1/1965 | Free |
| 3,581,062 | A | 5/1971 | Aston |
| 3,926,760 | A | 12/1975 | Allen et al. |
| 3,949,388 | A | 4/1976 | Fuller |
| 3,960,497 | A | 6/1976 | Acord et al. |
| 4,036,749 | A | 7/1977 | Anderson |
| 4,055,175 | A | 10/1977 | Clemens et al. |

(Continued)

FOREIGN PATENT DOCUMENTS

| | | |
|---|---|---|
| CN | 102307517 A | 1/2012 |
| CN | 102469941 A | 5/2012 |

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner* — Rajeev P Siripurapu
*Assistant Examiner* — Michael A Catina
(74) *Attorney, Agent, or Firm* — Sterne, Kessler, Goldstein & Fox P.L.L.C.

(57) ABSTRACT

Systems, devices and methods for monitoring analyte levels using a self-powered analyte sensor and associated sensor electronics are provided.

15 Claims, 13 Drawing Sheets

(56) References Cited

U.S. PATENT DOCUMENTS

| | | |
|---|---|---|
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,431,004 A | 2/1984 | Bessman et al. |
| 4,441,968 A | 4/1984 | Emmer et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,550,076 A | 10/1985 | Chikazawa et al. |
| 4,619,793 A | 10/1986 | Lee |
| 4,627,445 A | 12/1986 | Garcia et al. |
| 4,671,288 A | 6/1987 | Gough |
| 4,703,756 A | 11/1987 | Gough et al. |
| 4,711,245 A | 12/1987 | Higgins et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,820,399 A | 4/1989 | Senda et al. |
| 4,854,322 A | 8/1989 | Ash et al. |
| 4,871,351 A | 10/1989 | Feingold |
| 4,890,620 A | 1/1990 | Gough |
| 4,891,104 A | 1/1990 | Liston et al. |
| 4,897,162 A | 1/1990 | Lewandowski et al. |
| 4,925,268 A | 5/1990 | Iyer et al. |
| 4,953,552 A | 9/1990 | DeMarzo |
| 4,974,929 A | 12/1990 | Curry |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,165,407 A | 11/1992 | Wilson et al. |
| 5,200,051 A | 4/1993 | Cozzette et al. |
| 5,202,261 A | 4/1993 | Musho et al. |
| 5,202,317 A | 4/1993 | Bruice |
| 5,204,264 A | 4/1993 | Kaminer et al. |
| 5,210,778 A | 5/1993 | Massart |
| 5,217,966 A | 6/1993 | Bruice |
| 5,227,405 A | 7/1993 | Friedovich et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,715 A | 6/1994 | Berg |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,390,671 A | 2/1995 | Lord et al. |
| 5,391,250 A | 2/1995 | Cheney, II et al. |
| 5,408,999 A | 4/1995 | Singh et al. |
| 5,411,647 A | 5/1995 | Johnson et al. |
| 5,425,868 A | 6/1995 | Pedersen |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,466,575 A | 11/1995 | Cozzette et al. |
| 5,468,562 A | 11/1995 | Farivar et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,543,326 A | 8/1996 | Heller et al. |
| 5,552,997 A | 9/1996 | Massart |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,610,293 A | 3/1997 | Riley et al. |
| 5,628,310 A | 5/1997 | Rao et al. |
| 5,628,890 A | 5/1997 | Nigel et al. |
| 5,640,954 A | 6/1997 | Pfeiffer et al. |
| 5,651,869 A | 7/1997 | Yoshioka et al. |
| 5,653,239 A | 8/1997 | Pompei et al. |
| 5,665,222 A | 9/1997 | Heller et al. |
| 5,696,109 A | 12/1997 | Malfroy-Camine et al. |
| 5,711,001 A | 1/1998 | Bussan et al. |
| 5,711,861 A | 1/1998 | Ward et al. |
| 5,733,259 A | 3/1998 | Valcke et al. |
| 5,735,285 A | 4/1998 | Albert et al. |
| 5,771,890 A | 6/1998 | Tamada |
| 5,772,586 A | 6/1998 | Heinonen et al. |
| 5,791,344 A | 8/1998 | Schulman et al. |
| 5,807,375 A | 9/1998 | Gross et al. |
| 5,814,020 A | 9/1998 | Gross |
| 5,820,551 A | 10/1998 | Hill et al. |
| 5,820,570 A | 10/1998 | Erickson et al. |
| 5,822,715 A | 10/1998 | Worthington et al. |
| 5,858,001 A | 1/1999 | Tsais et al. |
| 5,882,494 A | 3/1999 | Van Antwerp |
| 5,899,855 A | 5/1999 | Brown |
| 5,906,921 A | 5/1999 | Ikeda et al. |
| 5,914,026 A | 6/1999 | Blubaugh et al. |
| 5,918,603 A | 7/1999 | Brown |
| 5,925,021 A | 7/1999 | Castellano et al. |
| 5,931,868 A | 8/1999 | Gross et al. |
| 5,935,224 A | 8/1999 | Svancarek et al. |
| 5,942,979 A | 8/1999 | Luppino |
| 5,947,957 A | 9/1999 | Morris |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,993,411 A | 11/1999 | Choi |
| 5,994,339 A | 11/1999 | Crapo et al. |
| 5,995,860 A | 11/1999 | Sun et al. |
| 5,997,501 A | 12/1999 | Gross et al. |
| 6,001,067 A | 12/1999 | Shults et al. |
| 6,011,077 A | 1/2000 | Muller |
| 6,023,629 A | 2/2000 | Tamada |
| 6,024,699 A | 2/2000 | Surwit et al. |
| 6,049,727 A | 4/2000 | Crothall |
| 6,071,391 A | 6/2000 | Gotoh et al. |
| 6,081,736 A | 6/2000 | Colvin et al. |
| 6,083,710 A | 7/2000 | Heller et al. |
| 6,084,093 A | 7/2000 | Riley et al. |
| 6,088,608 A | 7/2000 | Schulman et al. |

(56) References Cited

U.S. PATENT DOCUMENTS

| | | |
|---|---|---|
| 6,091,976 A | 7/2000 | Pfeiffer et al. |
| 6,093,172 A | 7/2000 | Funderburk et al. |
| 6,103,033 A | 8/2000 | Say et al. |
| 6,103,714 A | 8/2000 | Fridovich et al. |
| 6,110,155 A | 8/2000 | Baudino |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,122,536 A | 9/2000 | Sun et al. |
| 6,127,356 A | 10/2000 | Crapo et al. |
| 6,134,461 A | 10/2000 | Say et al. |
| 6,143,164 A | 11/2000 | Heller et al. |
| 6,144,837 A | 11/2000 | Quy |
| 6,144,869 A | 11/2000 | Berner et al. |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,186,982 B1 | 2/2001 | Gross et al. |
| 6,190,315 B1 | 2/2001 | Kost et al. |
| 6,200,265 B1 | 3/2001 | Walsh et al. |
| 6,212,416 B1 | 4/2001 | Ward et al. |
| 6,214,817 B1 | 4/2001 | Riley et al. |
| 6,219,574 B1 | 4/2001 | Cormier et al. |
| 6,233,471 B1 | 5/2001 | Berner et al. |
| 6,240,306 B1 | 5/2001 | Rohrscheib et al. |
| 6,245,758 B1 | 6/2001 | Stem et al. |
| 6,248,067 B1 | 6/2001 | Causey, III et al. |
| 6,254,586 B1 | 7/2001 | Mann et al. |
| 6,267,002 B1 | 7/2001 | Ehwald et al. |
| 6,268,161 B1 | 7/2001 | Han et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,298,254 B2 | 10/2001 | Tamada |
| 6,299,347 B1 | 10/2001 | Pompei |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,331,244 B1 | 12/2001 | Lewis et al. |
| 6,338,790 B1 | 1/2002 | Feldman et al. |
| 6,343,225 B1 | 1/2002 | Clark, Jr. |
| 6,348,640 B1 | 2/2002 | Navot et al. |
| 6,359,444 B1 | 3/2002 | Grimes |
| 6,360,888 B1 | 3/2002 | McIvor et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,372,045 B1 | 4/2002 | McCabe et al. |
| 6,377,828 B1 | 4/2002 | Chaiken et al. |
| 6,377,894 B1 | 4/2002 | Deweese et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,403,788 B1 | 6/2002 | Meunier et al. |
| 6,405,066 B1 | 6/2002 | Essenpreis et al. |
| 6,413,393 B1 | 7/2002 | Van Antwerp et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,434,409 B1 | 8/2002 | Pfeiffer et al. |
| 6,436,255 B2 | 8/2002 | Yamamoto et al. |
| 6,438,414 B1 | 8/2002 | Conn et al. |
| 6,440,068 B1 | 8/2002 | Brown et al. |
| 6,445,374 B2 | 9/2002 | Albert et al. |
| 6,448,239 B1 | 9/2002 | Groves et al. |
| 6,461,496 B1 | 10/2002 | Feldman et al. |
| 6,466,810 B1 | 10/2002 | Ward et al. |
| 6,471,689 B1 | 10/2002 | Joseph et al. |
| 6,475,181 B1 | 11/2002 | Potter et al. |
| 6,475,196 B1 | 11/2002 | Vachon |
| 6,477,395 B2 | 11/2002 | Schulman et al. |
| 6,477,891 B2 | 11/2002 | Ehwald et al. |
| 6,478,736 B1 | 11/2002 | Mault |
| 6,479,477 B1 | 11/2002 | Crapo et al. |
| 6,482,176 B1 | 11/2002 | Wich |
| 6,484,046 B1 | 11/2002 | Say et al. |
| 6,491,657 B2 | 12/2002 | Rowe et al. |
| 6,493,069 B1 | 12/2002 | Nagashimada et al. |
| 6,497,729 B1 | 12/2002 | Moussy et al. |
| 6,503,381 B1 | 1/2003 | Gotoh et al. |
| 6,508,785 B1 | 1/2003 | Eppstein |
| 6,512,939 B1 | 1/2003 | Colvin et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,525,041 B1 | 2/2003 | Neumann et al. |
| 6,530,915 B1 | 3/2003 | Eppstein et al. |
| 6,540,891 B1 | 4/2003 | Stewart et al. |
| 6,541,490 B1 | 4/2003 | Campbell et al. |
| 6,544,212 B2 | 4/2003 | Galley et al. |
| 6,544,975 B1 | 4/2003 | Crapo et al. |
| 6,546,268 B1 | 4/2003 | Ishikawa et al. |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,573,257 B2 | 6/2003 | Malfroy-Camine et al. |
| 6,574,490 B2 | 6/2003 | Abbink et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,589,948 B1 | 7/2003 | Malfroy-Camine et al. |
| 6,591,125 B1 | 7/2003 | Buse et al. |
| 6,591,126 B2 | 7/2003 | Roeper et al. |
| 6,592,745 B1 | 7/2003 | Feldman et al. |
| 6,592,746 B1 | 7/2003 | Schmid-Schoenbein et al. |
| 6,595,919 B2 | 7/2003 | Berner et al. |
| 6,599,407 B2 | 7/2003 | Taniike et al. |
| 6,600,997 B2 | 7/2003 | Deweese et al. |
| 6,602,678 B2 | 8/2003 | Kwon et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,620,123 B1 | 9/2003 | Mitragotri et al. |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,676,816 B2 | 1/2004 | Mao et al. |
| 6,679,841 B2 | 1/2004 | Bojan et al. |
| 6,685,699 B1 | 2/2004 | Eppstein et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,706,049 B2 | 3/2004 | Moerman |
| 6,723,077 B2 | 4/2004 | Pickup et al. |
| 6,730,200 B1 | 5/2004 | Stewart et al. |

(56) References Cited

U.S. PATENT DOCUMENTS

| | | |
|---|---|---|
| 6,733,446 B2 | 5/2004 | Lebel et al. |
| 6,736,957 B1 | 5/2004 | Forrow et al. |
| 6,740,075 B2 | 5/2004 | Lebel et al. |
| 6,740,215 B1 | 5/2004 | Nakaminami et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,770,729 B2 | 8/2004 | Van Antwerp |
| 6,773,671 B1 | 8/2004 | Lewis et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,835,387 B2 | 12/2004 | Herrmann |
| 6,837,988 B2 | 1/2005 | Leong et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,885,196 B2 | 4/2005 | Taniike et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,971,999 B2 | 12/2005 | Py et al. |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,016,713 B2 | 3/2006 | Gardner et al. |
| 7,022,072 B2 | 4/2006 | Fox et al. |
| 7,022,219 B2 | 4/2006 | Mansouri et al. |
| 7,024,245 B2 | 4/2006 | Lebel et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,134,999 B2 | 11/2006 | Brauker et al. |
| 7,136,689 B2 | 11/2006 | Shults et al. |
| 7,153,265 B2 | 12/2006 | Vachon |
| 7,167,818 B2 | 1/2007 | Brown |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,978 B2 | 6/2007 | Tapsak et al. |
| 7,258,673 B2 | 8/2007 | Racchini et al. |
| 7,267,665 B2 | 9/2007 | Steil et al. |
| 7,276,029 B2 | 10/2007 | Goode et al. |
| 7,278,983 B2 | 10/2007 | Ireland et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,387,010 B2 | 6/2008 | Sunshine |
| 7,402,153 B2 | 7/2008 | Steil et al. |
| 7,404,796 B2 | 7/2008 | Ginsberg |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,509,153 B2 | 3/2009 | Blank et al. |
| 7,519,408 B2 | 4/2009 | Rasdal et al. |
| 7,547,281 B2 | 6/2009 | Hayes et al. |
| 7,569,030 B2 | 8/2009 | Lebel et al. |
| 7,583,990 B2 | 9/2009 | Goode et al. |
| 7,591,801 B2 | 9/2009 | Brauker et al. |
| 7,599,726 B2 | 10/2009 | Goode et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbies et al. |
| 7,651,596 B2 | 1/2010 | Petisce et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,697,967 B2 | 4/2010 | Stafford |
| 7,699,775 B2 | 4/2010 | Desai et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,736,310 B2 | 6/2010 | Taub et al. |
| 7,766,829 B2 | 8/2010 | Sloan et al. |
| 7,771,352 B2 | 8/2010 | Shults et al. |
| 7,774,145 B2 | 8/2010 | Bruaker et al. |
| 7,778,680 B2 | 8/2010 | Goode, Jr. et al. |
| 7,778,795 B2 | 8/2010 | Fukushima et al. |
| 7,826,981 B2 | 11/2010 | Goode, Jr. et al. |
| 7,866,026 B1 | 1/2011 | Wang et al. |
| 7,882,611 B2 | 2/2011 | Shah et al. |
| 7,889,069 B2 | 2/2011 | Fifolt et al. |
| 7,899,511 B2 | 3/2011 | Shults et al. |
| 7,905,833 B2 | 3/2011 | Brister et al. |
| 7,911,010 B2 | 3/2011 | Stetter |
| 7,914,450 B2 | 3/2011 | Goode, Jr. et al. |
| 7,938,797 B2 | 5/2011 | Estes |
| 7,954,385 B2 | 6/2011 | Raisanen |
| 7,974,672 B2 | 7/2011 | Shults et al. |
| 8,216,138 B1 | 7/2012 | McGarraugh et al. |
| 8,282,549 B2 | 10/2012 | Brauker et al. |
| 2001/0020125 A1 | 9/2001 | Kurnik et al. |
| 2001/0039393 A1 | 11/2001 | Mori et al. |
| 2001/0041830 A1 | 11/2001 | Varalli et al. |
| 2002/0006634 A1 | 1/2002 | Han et al. |
| 2002/0019022 A1 | 2/2002 | Dunn et al. |
| 2002/0023852 A1 | 2/2002 | McIvor et al. |
| 2002/0026110 A1 | 2/2002 | Parris et al. |
| 2002/0042090 A1 | 4/2002 | Heller et al. |
| 2002/0042407 A1 | 4/2002 | Fridovich et al. |
| 2002/0055711 A1 | 5/2002 | Lavi et al. |
| 2002/0068860 A1 | 6/2002 | Clark |

(56) References Cited

U.S. PATENT DOCUMENTS

| | | |
|---|---|---|
| 2002/0082490 A1 | 6/2002 | Roeper et al. |
| 2002/0082543 A1 | 6/2002 | Park et al. |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0161288 A1 | 10/2002 | Shin et al. |
| 2002/0168290 A1 | 11/2002 | Yuzhakov et al. |
| 2002/0169635 A1 | 11/2002 | Shillingburg |
| 2002/0183604 A1 | 12/2002 | Gowda et al. |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0031699 A1 | 2/2003 | Van Antwerp |
| 2003/0032867 A1 | 2/2003 | Crothall et al. |
| 2003/0032874 A1 | 2/2003 | Rhodes et al. |
| 2003/0004213 A1 | 3/2003 | Mao et al. |
| 2003/0045798 A1 | 3/2003 | Hular et al. |
| 2003/0055032 A1 | 3/2003 | Groves et al. |
| 2003/0060692 A1 | 3/2003 | Ruchti et al. |
| 2003/0065254 A1 | 4/2003 | Schulman et al. |
| 2003/0065308 A1 | 4/2003 | Lebel et al. |
| 2003/0069281 A1 | 4/2003 | Fridovich et al. |
| 2003/0077702 A1 | 4/2003 | Shah et al. |
| 2003/0077772 A1 | 4/2003 | Shah et al. |
| 2003/0078560 A1 | 4/2003 | Miller et al. |
| 2003/0099682 A1 | 5/2003 | Moussy et al. |
| 2003/0100821 A1 | 5/2003 | Heller et al. |
| 2003/0118577 A1 | 6/2003 | Weill et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0190341 A1 | 10/2003 | Shalaby et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0199837 A1 | 10/2003 | Vachon |
| 2003/0208113 A1 | 11/2003 | Mault et al. |
| 2003/0212317 A1 | 11/2003 | Kovatchev et al. |
| 2003/0212346 A1 | 11/2003 | Yuzhakov et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0028612 A1 | 2/2004 | Singaram et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0063167 A1 | 4/2004 | Kaastrup et al. |
| 2004/0064068 A1 | 4/2004 | DeNuzzio et al. |
| 2004/0064133 A1 | 4/2004 | Miller et al. |
| 2004/0074785 A1 | 4/2004 | Holker et al. |
| 2004/0096959 A1 | 5/2004 | Steine et al. |
| 2004/0099529 A1 | 5/2004 | Mao et al. |
| 2004/0106858 A1 | 6/2004 | Say et al. |
| 2004/0110722 A1 | 6/2004 | Ørnberg et al. |
| 2004/0116332 A1 | 6/2004 | Ørnberg et al. |
| 2004/0116847 A1 | 6/2004 | Wall |
| 2004/0122353 A1 | 6/2004 | Shahmirian et al. |
| 2004/0116866 A1 | 7/2004 | Gorman et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0146909 A1 | 7/2004 | Duong et al. |
| 2004/0147996 A1 | 7/2004 | Miazga et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0223985 A1 | 11/2004 | Dunfiled et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0249254 A1 | 12/2004 | Racchini et al. |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0054908 A1 | 3/2005 | Blank et al. |
| 2005/0054909 A1 | 3/2005 | Petisce et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0096520 A1 | 5/2005 | Maekawa et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154271 A1 | 7/2005 | Rasdal et al. |
| 2005/0173245 A1 | 8/2005 | Feldman et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0214892 A1 | 9/2005 | Kovatchev et al. |
| 2005/0215871 A1 | 9/2005 | Feldman et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |

(56) References Cited

U.S. PATENT DOCUMENTS

| | | |
|---|---|---|
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister |
| 2006/0091006 A1 | 5/2006 | Wang et al. |
| 2006/0142651 A1 | 6/2006 | Brister et al. |
| 2006/0155180 A1 | 7/2006 | Brister et al. |
| 2006/0166629 A1 | 7/2006 | Reggiardo |
| 2006/0170535 A1 | 8/2006 | Watters et al. |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbies et al. |
| 2006/0183985 A1 | 8/2006 | Brister et al. |
| 2006/0189863 A1 | 8/2006 | Peyser et al. |
| 2006/0193375 A1 | 8/2006 | Lee |
| 2006/0219576 A1 | 10/2006 | Jina et al. |
| 2006/0222566 A1 | 10/2006 | Brauker et al. |
| 2006/0224109 A1 | 10/2006 | Steil et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247985 A1 | 11/2006 | Liamos et al. |
| 2006/0258929 A1 | 11/2006 | Goode et al. |
| 2006/0272652 A1 | 12/2006 | Stocker et al. |
| 2006/0281985 A1 | 12/2006 | Ward et al. |
| 2007/0000163 A1 | 1/2007 | Kamath et al. |
| 2007/0000273 A1 | 2/2007 | Stafford |
| 2007/0032717 A1 | 2/2007 | Brister et al. |
| 2007/0033074 A1 | 2/2007 | Nitzan et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0095661 A1 | 5/2007 | Wang et al. |
| 2007/0106135 A1 | 5/2007 | Sloan et al. |
| 2007/0106175 A1* | 5/2007 | Uchiyama ............ A61B 1/041 |
| | | 600/564 |
| 2007/0108048 A1 | 5/2007 | Wang et al. |
| 2007/0124002 A1 | 5/2007 | Estes et al. |
| 2007/0129602 A1 | 6/2007 | Bettesh et al. |
| 2007/0149875 A1 | 6/2007 | Quyang et al. |
| 2007/0156033 A1 | 7/2007 | Causey, III et al. |
| 2007/0163880 A1 | 7/2007 | Woo et al. |
| 2007/0163894 A1 | 7/2007 | Wang et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0197957 A1 | 8/2007 | Hunter et al. |
| 2007/0199818 A1 | 8/2007 | Petyt et al. |
| 2007/0203407 A1 | 8/2007 | Hoss et al. |
| 2007/0203966 A1 | 8/2007 | Brauker et al. |
| 2007/0219496 A1 | 9/2007 | Kamen et al. |
| 2007/0227911 A1 | 10/2007 | Wang et al. |
| 2007/0232878 A1 | 10/2007 | Kovatchev et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0249922 A1 | 10/2007 | Peyser et al. |
| 2007/0255321 A1 | 11/2007 | Gerber et al. |
| 2007/0258395 A1 | 11/2007 | Jollota et al. |
| 2007/0282299 A1 | 12/2007 | Hellwig |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0033268 A1 | 2/2008 | Stafford |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0066305 A1 | 3/2008 | Wang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097246 A1 | 4/2008 | Stafford |
| 2008/0097289 A1 | 4/2008 | Steil et al. |
| 2008/0102441 A1 | 5/2008 | Chen et al. |
| 2008/0108942 A1 | 5/2008 | Brister et al. |
| 2008/0114280 A1 | 5/2008 | Stafford |
| 2008/0119703 A1 | 5/2008 | Brister et al. |
| 2008/0119707 A1 | 5/2008 | Stafford |
| 2008/0119708 A1 | 5/2008 | Budiman |
| 2008/0129486 A1* | 6/2008 | Jeckelmann ......... A61B 5/0002 |
| | | 340/539.12 |
| 2008/0139910 A1 | 6/2008 | Mastrototaro et al. |
| 2008/0148873 A1 | 6/2008 | Wang |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0172205 A1 | 7/2008 | Breton et al. |
| 2008/0177149 A1 | 7/2008 | Weinert et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0019493 A1 | 8/2008 | Brister et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0314395 A1 | 8/2008 | Kovatchev et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234943 A1 | 9/2008 | Ray et al. |
| 2008/0242961 A1 | 10/2008 | Brister et al. |
| 2008/0242963 A1 | 10/2008 | Essenpreis et al. |

(56) References Cited

U.S. PATENT DOCUMENTS

| | | |
|---|---|---|
| 2008/0255434 A1 | 10/2008 | Hayter et al. |
| 2008/0255437 A1 | 10/2008 | Hayter |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300476 A1 | 12/2008 | Stafford |
| 2008/0300572 A1 | 12/2008 | Rankers et al. |
| 2008/0306368 A1 | 12/2008 | Goode et al. |
| 2008/0306434 A1 | 12/2008 | Dobbies et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012377 A1 | 1/2009 | Jennewine et al. |
| 2009/0012379 A1 | 1/2009 | Goode et al. |
| 2009/0018424 A1 | 1/2009 | Kamath et al. |
| 2009/0018425 A1 | 1/2009 | Quyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054748 A1 | 2/2009 | Feldman et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0088614 A1 | 4/2009 | Taub |
| 2009/0099436 A1 | 4/2009 | Brister et al. |
| 2009/0105560 A1 | 4/2009 | Solomon |
| 2009/0105569 A1 | 4/2009 | Stafford |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0171182 A1 | 7/2009 | Stafford |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0253973 A1 | 10/2009 | Bashan et al. |
| 2009/0259118 A1 | 10/2009 | Feldman et al. |
| 2009/0287073 A1 | 11/2009 | Boock et al. |
| 2009/0287074 A1 | 11/2009 | Shults et al. |
| 2009/0294277 A1 | 12/2009 | Thomas et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbies et al. |
| 2010/0081909 A1 | 4/2010 | Budiman et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121167 A1 | 5/2010 | McGarraugh et al. |

(56) References Cited

U.S. PATENT DOCUMENTS

| | | |
|---|---|---|
| 2010/0121169 A1 | 5/2010 | Petisce et al. |
| 2010/0141656 A1 | 6/2010 | Krieftewirth |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213057 A1 | 8/2010 | Feldman et al. |
| 2010/0230285 A1 | 9/2010 | Hoss et al. |
| 2010/0234710 A1 | 9/2010 | Budiman et al. |
| 2010/0265073 A1 | 10/2010 | Harper et al. |
| 2010/0274515 A1 | 10/2010 | Hoss et al. |
| 2010/0277119 A1 | 11/2010 | Montague et al. |
| 2010/0277342 A1 | 11/2010 | Sicurello et al. |
| 2010/0280441 A1 | 11/2010 | Willinska et al. |
| 2010/0280782 A1 | 11/2010 | Harper et al. |
| 2010/0312176 A1 | 12/2010 | Lauer et al. |
| 2010/0312314 A1 | 12/2010 | Ice et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0324853 A1 | 12/2010 | Wang et al. |
| 2010/0326842 A1 | 12/2010 | Mazza et al. |
| 2010/0331646 A1 | 12/2010 | Hoss et al. |
| 2010/0331653 A1 | 12/2010 | Stafford |
| 2011/0021889 A1 | 1/2011 | Hoss et al. |
| 2011/0184258 A1 | 1/2011 | Stafford |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0054275 A1 | 3/2011 | Stafford |
| 2011/0060196 A1 | 3/2011 | Stafford |
| 2011/0073475 A1 | 3/2011 | Kastanos et al. |
| 2011/0077490 A1 | 3/2011 | Simpson et al. |
| 2011/0077494 A1 | 3/2011 | Doniger et al. |
| 2011/0081726 A1 | 4/2011 | Berman et al. |
| 2011/0082484 A1 | 4/2011 | Saravia et al. |
| 2011/0105873 A1 | 5/2011 | Feldman et al. |
| 2011/0106126 A1 | 5/2011 | Love et al. |
| 2011/0144463 A1 | 6/2011 | Pesach et al. |
| 2011/0148905 A1 | 6/2011 | Simmons et al. |
| 2011/0152637 A1 | 6/2011 | Kateraas et al. |
| 2011/0160553 A1 | 6/2011 | Talbot et al. |
| 2011/0319733 A1 | 6/2011 | Stafford |
| 2011/0184268 A1 | 7/2011 | Taub |
| 2011/0190603 A1 | 8/2011 | Stafford |
| 2011/0191044 A1 | 8/2011 | Stafford |
| 2011/0193704 A1 | 8/2011 | Harper et al. |
| 2011/0208027 A1 | 8/2011 | Wagner et al. |
| 2011/0208155 A1 | 8/2011 | Palerm et al. |
| 2011/0213225 A1 | 9/2011 | Bernstein et al. |
| 2011/0257495 A1 | 10/2011 | Hoss et al. |
| 2011/0257895 A1 | 10/2011 | Brauker et al. |
| 2011/0263958 A1 | 10/2011 | Brauker et al. |
| 2011/0288574 A1 | 11/2011 | Curry et al. |
| 2011/0031973 A1 | 12/2011 | Woodruff et al. |
| 2011/0319729 A1 | 12/2011 | Donnay et al. |
| 2011/0320130 A1 | 12/2011 | Valdes et al. |
| 2012/0010642 A1 | 1/2012 | Lee et al. |
| 2012/0041291 A1 | 2/2012 | Ferren et al. |
| 2012/0078071 A1 | 3/2012 | Bohm et al. |
| 2012/0088995 A1 | 4/2012 | Fennell et al. |
| 2012/0108931 A1 | 5/2012 | Taub |
| 2012/0108934 A1 | 5/2012 | Valdes et al. |
| 2012/0123690 A1 | 5/2012 | Wang et al. |
| 2012/0157801 A1 | 6/2012 | Hoss et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0179015 A1 | 7/2012 | Mann et al. |
| 2012/0215462 A1 | 8/2012 | Goode et al. |
| 2012/0296187 A1 | 11/2012 | Henning et al. |
| 2013/0015063 A1 | 1/2013 | Tsugawa et al. |
| 2013/0035575 A1 | 2/2013 | Mayou et al. |
| 2013/0184547 A1 | 7/2013 | Taub et al. |
| 2014/0121480 A1 | 5/2014 | Budiman et al. |
| 2015/0054468 A1* | 2/2015 | Nikonov ............... H01M 8/16 320/137 |

FOREIGN PATENT DOCUMENTS

| | | |
|---|---|---|
| CN | 102473276 A | 5/2012 |
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1153571 | 11/2001 |
| EP | 1568309 | 8/2005 |
| EP | 1746928 | 1/2012 |
| FR | 2652736 A1 | 4/1991 |
| KR | 20130067387 A | 6/2013 |
| RU | 2233111 C1 | 7/2004 |
| WO | WO-1994/010560 | 5/1994 |
| WO | WO-1995/031197 | 11/1995 |
| WO | WO-1996/025089 | 8/1996 |
| WO | WO-1996/035370 | 11/1996 |
| WO | WO-1998/017199 | 4/1998 |
| WO | WO-1998/043637 | 10/1998 |
| WO | WO-1999/047471 | 9/1999 |
| WO | WO-2000/049940 | 8/2000 |
| WO | WO-2000/059370 | 10/2000 |
| WO | WO-2000/074753 | 12/2000 |
| WO | WO-2000/075144 | 12/2000 |
| WO | WO-2000/078293 | 12/2000 |
| WO | WO-2001/052935 | 7/2001 |
| WO | WO-2001/054753 | 8/2001 |
| WO | WO-2002/016905 | 2/2002 |
| WO | WO-2002/039086 | 5/2002 |
| WO | WO-2002/044187 | 6/2002 |
| WO | WO-2003/006091 | 1/2003 |
| WO | WO-2003/090509 | 4/2003 |
| WO | WO-2003/053503 | 7/2003 |
| WO | WO-2003/063925 | 8/2003 |
| WO | WO-2003/071930 | 9/2003 |
| WO | WO-2003/076893 | 9/2003 |
| WO | WO-2003/082091 | 10/2003 |
| WO | WO-2003/103763 | 12/2003 |
| WO | WO-2004/007756 | 1/2004 |
| WO | WO-2004/028337 | 4/2004 |
| WO | WO-2006/024671 | 3/2006 |
| WO | WO-2007/007459 | 1/2007 |
| WO | WO-2008/086541 | 7/2008 |
| WO | WO-2008/043637 | 10/2008 |
| WO | 2010099335 A1 | 9/2010 |
| WO | WO-2010/099335 | 9/2010 |
| WO | 2012048168 A2 | 4/2012 |
| WO | WO-2010/077329 | 7/2012 |

OTHER PUBLICATIONS

Banile, J., et al., Glucose Measurement in Patients with Diabtes Mellitus with Dermal Interstitial Fluid, *J. Lab. Clin. Med.*, vol. 130, No. 4, 1997, pp. 436-431.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.

(56) References Cited

OTHER PUBLICATIONS

Bremer, T. M., et al., "Benchmark Data from the Literature for Evaluation of New Glucose Sensing Technologies", *Diabetes Technology & Therapeutics*, vol. 3, No. 3, 2001, pp. 409-418.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Csoregi, E., et al., "Design, Characterization, and One-Point in Vivo Calibration of a Subcutaneously Implanted Glucose Electrode", *Analytical Chemistry*, vol. 66, No. 19, 1994, pp. 3131-3138.

DIRECNET Study Group, "Accuracy of the Gluco Watch G2 Biographer and the Continuous Glucose Monitoring System During Hyoglycemia", *Diabetes Care*, vol. 27, No. 3, 2004, pp. 722-726.

Durand, S., et al., "Current-Induced Vasodilation During Water Iontophoresis (5 min, 0.10 mA) Is Delayed From Current Onset and Involves Aspirin Sensitive Mechanisms", *Journal of Vascular Research*, vol. 39, 2002, pp. 59-71.

Feldman, B., et al., "A Continuous Glucose Sensor Based on Wired EnzymeTM Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*.

Grossmann, M., et al., "The Effect of Iontophoresis on the Cutaneous Vasculature: Evidence for Current-Induced Hyperemia", *Microvascular Research*, vol. 50, 1995, pp. 444-452.

Heller, A., et al., "Amperometric Biosensors Based on Three-Dimensional Hydrogel-Forming Epoxy Networks", *Sensors and Actuators B*, vol. 13-14, 1993, pp. 180-183.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Jobst, G., et al., "Thin-Film Microbiosensors for Glucose-Lactate Monitoring", *Analytical Chemistry*, vol. 68, No. 18, 1996, pp. 3173-3179.

Johnson, P. C., "Peripheral Circulation", John Wiley & Sons, 1978, pp. 198.

Jungheim, K., et al., "How Rapid Does Glucose Concentration Change in Daily Life of Patients with Type 1 Diabetes?", pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Lortz, J., et al., "What is Bluetooth? We Explain the Newest Short-Range Connectivity Technology", Smart Computing Learning Series, *Wireless Computing*, vol. 8, Issue 5, 2002, pp. 72-74.

Maidan, R., et al., "Elimination of Electrooxidizable Interferant-Produced Currents in Amperometric Biosensors", *Analytical Chemistry*, vol. 64, No. 23, 1992, pp. 2889-2896.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

Mauras, N., et al., "Lack of Accuracy of Continuous Glucose Sensors in Healthy, Nondiabetic Children: Results of the Diabetes Research in Children Network (DirecNet) Accuracy Study," *Journal of Pediatrics*, 2004, pp. 770-775.

McGarraugh, G., et al., "Glucose Measurements Using Blood Extracted from the Forearm and the Finger", TheraSense, Inc., 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Metzger, M., et al., "Reproducibility of Glucose Measurements Using the Glucose Sensor", *Diabetes Care*, vol. 25, No. 6, 2002, pp. 1185-1191.

Monsod, T. P., et al., "Do Sensor Glucose Levels Accurately Predict Plasma Glucose Concentrations During Hypoglycemia and Hyperinsulinemia?" *Diabetes Care*, vol. 25, No. 5, 2002, pp. 889-893.

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Mougiakakou, et al., "A Real Time Simulation Model of Glucose-Insulin Metabolism for Type 1 Diabetes Patients", *Proceedings of the 2005 IEEE*, 2005, pp. 298-301.

Panteleon, A. E., et al., "The Role of the Independent Variable to Glucose Sensor Calibration", *Diabetes Technology & Therapeutics*, vol. 5, No. 3, 2003, pp. 401-410.

Parker, R., et al., "Robust $H^\infty$ Glucose Control in Diabetes Using a Physiological Model", *AIChE Journal*, vol. 46, No. 12, 2000, pp. 2537-2549.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

(56) References Cited

OTHER PUBLICATIONS

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sternberg, R., et al., "Study and Development of Multilayer Needle-Typ Glucose Microsensors", *Biosensors*, vol. 4, 1988, pp. 27-40.
Thompson, M., et al., "In Vivo Probes: Problems and Perspectives", *Clinical Biochemistry*, vol. 19, 1986, pp. 255-261.
Tsalikian, E., et al., "Accuracy of the GlucoWatch G2® Biographer and the Continuous Glucose Monitoring System During Hypoglycemia: Experience of the Diabetes Research in Children Network", *Diabetes Care*, vol. 27, No. 3, 2004, pp. 722-726.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.
Velho, G., et al., "Strategies for Calibrating a Subcutaneous Glucose Sensor", *Biomedica Biochimica Acta*, vol. 48, 1989, pp. 957-964.
Wilson, G. S., et al., "Progress Toward the Development of an Implantable Glucose", *Clinical Chemistry*, vol. 38, No. 9, 1992, pp. 1613-1617.
PCT Application No. PCT/US2014/063316, International Search Report and Written Opinion of the International Searching Authority dated Mar. 24, 2015.
Ali, S., "Finite Element Modeling of Dermally-Implanted Enzymatic Microparticle Glucose Sensors", Thesis Submitted to the Office of Graduate Studies of Texas A&M University, 2010.
Hanashi, T. et al., "BioCapacitor—A Novel Category of Biosensor," Biosensors and Bioelectronics, Elsevier BV, NL, vol. 24, No. 7, Mar. 15, 2009, pp. 1837-1842, XP025958941, ISSN: 0956-5663, DOI: 10.1016/J.BIOS.2008.09.014, retrieved on Sep. 24, 2008.
Partial Supplementary European Search Report issued in EP Patent Application No. 14877021.7 dated Aug. 1, 2017.
Office Action issued in corresponding RU Patent Application No. 2016131308 dated Apr. 4, 2018, with English Translation.
Search Report issued in corresponding RU Patent Application No. 2016131308 dated Apr. 4, 2018, with English Translation.
Notification of First Office Action issued in corresponding Chinese Patent Application No. 2014800716857 dated Jun. 27, 2018, includes English Translation.
Hanashi, Takuya et al., "BioCapacitor—A Novel Category of Biosensor," Biosensors and Bioelectronics, No. 24, pp. 1838-1842, published Sep. 24, 2008.

\* cited by examiner

SELF-POWERED ANALYTE SENSOR AND DEVICES USING THE SAME

RELATED APPLICATION

The present application claims priority under 35 U.S.C. § 119(e) to U.S. Provisional Application No. 61/922,404 filed Dec. 31, 2013, entitled "Self-Powered Analyte Sensor and Devices Using the Same," the disclosure of which is incorporated herein by reference for all purposes.

BACKGROUND

The detection and/or monitoring of glucose levels or other analytes, such as lactate, oxygen, A1C, or the like, in certain individuals is vitally important to their health. For example, the monitoring of glucose is particularly important to individuals with diabetes. Diabetics generally monitor glucose levels to determine if their glucose levels are being maintained within a clinically safe range, and may also use this information to determine if and/or when insulin is needed to reduce glucose levels in their bodies or when additional glucose is needed to raise the level of glucose in their bodies.

Devices have been developed for the automatic monitoring of analyte(s), such as glucose, in bodily fluid such as in the blood stream or in interstitial fluid ("ISF"), or other biological fluid. Some of these analyte measuring devices are configured so that at least a portion of the devices are positioned below a skin surface of a user, e.g., in a blood vessel or in the subcutaneous tissue of a user, so that the monitoring is accomplished in vivo.

Measurement of analyte(s), such as glucose, by a monitoring device requires power. Current monitoring devices require an external power source to power the sensing circuitry and store the measured values in a memory for later retrieval by a display device.

SUMMARY

An analyte monitoring device in certain embodiments includes a self-powered analyte sensor having at least a portion in fluid contact with interstitial fluid under a skin surface, and sensor electronics operatively coupled to the self-powered analyte sensor, configured to receive signals generated by the self-powered analyte sensor, and to communicate data corresponding to analyte level monitored by the self-powered analyte sensor, the sensor electronics including: a buffering circuit operatively coupled to the self-powered analyte sensor for receiving the generated signals from the self-powered analyte sensor, and a radio frequency identification device (RFID) circuit operatively coupled to the buffering circuit and configured to communicate data corresponding to the generated signals associated with the monitored analyte level.

An analyte monitoring device in certain embodiments of the present disclosure includes a self-powered analyte sensor, and sensor electronics operatively coupled to the self-powered analyte sensor configured to receive signals generated by the self-powered analyte sensor and to communicate data corresponding to analyte level monitored by the self-powered analyte sensor, where the sensor electronics transitions from an inactive state to an active state when powered by a remote power source and upon receipt of a query signal from the remote power source, and in response to the query signal, communicates data corresponding to the generated signals associated with the monitored analyte level to the remote power source.

In certain embodiments, the self-powered analyte sensor is configured to continuously generate signals corresponding to monitored analyte level when in fluid contact with interstitial fluid.

In certain embodiments, the self-powered analyte sensor generates the signals corresponding to monitored analyte level when the sensor electronics are in the inactive state.

In certain embodiments, the sensor electronics are not operational when in the inactive state.

In certain embodiments, the sensor electronics include a buffering circuit operatively coupled to the self-powered analyte sensor for receiving the generated signals from the self-powered analyte sensor.

In certain embodiments, the sensor electronics includes a radio frequency identification device (RFID) circuit operatively coupled to the buffering circuit and configured to communicate data corresponding to the generated signals associated with the monitored analyte level.

In certain embodiments, the analyte monitoring device further includes a housing enclosing the self-powered sensor and the sensor electronics, wherein the housing is sealed to inhibit moisture from entering the housing.

In certain embodiments, the query signal includes an RFID signal.

In certain embodiments, the sensor electronics transition from the active state to the inactive state when the sensor electronics is not within the range of the remote power source.

In certain embodiments, the self-powered sensor is configured to generate the signals when in contact with the interstitial fluid and when the sensor electronics is in the inactive state.

In certain embodiments, the analyte monitoring device includes a housing enclosing the self-powered sensor and the sensor electronics, the housing including one or more mechanical components for physically detachably engaging with a remote device.

In certain embodiments, the remote device includes the remote power source.

In certain embodiments, the one or more mechanical components include one or more of a releasable latch, a releasable arm, or a releasable lock.

An analyte monitoring device, in certain embodiments, includes a self-powered analyte sensor having at least a portion in fluid contact with interstitial fluid under a skin surface, and sensor electronics operatively coupled to the self-powered analyte sensor configured to receive signals generated by the self-powered analyte sensor and to communicate data corresponding to analyte level monitored by the self-powered analyte sensor, the sensor electronics including: a buffering circuit operatively coupled to the self-powered analyte sensor for receiving the generated signals from the self-powered analyte sensor; and a radio frequency identification device (RFID) circuit operatively coupled to the buffering circuit and configured to communicate data corresponding to the generated signals associated with the monitored analyte level, where the sensor electronics transitions from an inactive state to an active state when powered by a remote power source and upon receipt of a query signal from the remote power source, and in response to the query signal, communicates data corresponding to the generated signals associated with the monitored analyte level to the remote power source.

In certain embodiments of the present disclosure, using the signals generated by the oxidation reaction of the self-powered sensor accumulated over time and stored in a capacitor device, sufficient charge is accumulated to drive the sensor electronics for processing signals related to the monitored analyte level, including storing, filtering, processing and communicating to a remote location. In this manner, sensor electronics coupled to the self-powered analyte sensor does not require a separate power source such as a battery to power the sensor electronics for processing signals related to the monitored analyte level including storing the generated and processed signals.

In some embodiments, a remote device such as a display device is configured to generate a magnetic field which, when positioned in close proximity to the sensor electronics, latches a switch in the sensor electronics to drive the charge stored in the sensor electronics capacitor device (generated from the self-powered sensor) to connect the remaining portions of the sensor electronics, effectively powering the sensor electronics solely from the charge stored in the capacitor that was generated by the self-powered sensor.

In a further embodiment, the self-powered sensor and sensor electronics are provided in a sealed housing and which does not include electronic components susceptible to sterilization processes for the sensor, and that would otherwise degrade or damage such electronic components. In this manner, in certain embodiments, a single enclosed housing including sensor electronics and the analyte sensor are provided which can be sterilized together using a single sterilization technique without damaging or degrading the components of the on body sensor device.

A method of monitoring analyte levels, in certain embodiments, includes transcutaneously positioning an analyte sensor in fluid contact with interstitial fluid under a skin surface, accumulating charge for a predetermined time period in a capacitor device in sensor electronics, the capacitor device in signal communication with the analyte sensor and receiving signals from the analyte sensor, detecting a magnetic field exceeding a threshold level, latching a switch provided in the sensor electronics to couple the capacitor device in the sensor electronics to sensor signal processing components when the detected magnetic field exceeds the threshold level, and connecting the capacitor device to the sensor signal processing components to provide power to the sensor signals processing components with the accumulated charge in the capacitor device.

A device for monitoring analyte level, in certain embodiments, includes an analyte sensor for transcutaneous positioning in fluid contact with interstitial fluid, sensor electronics including: sensor signal processing components, a capacitor device operatively coupled to the analyte sensor to accumulate charge for a predetermined time period, and a switch configured to latch, when a magnetic field exceeding a threshold level is detected, to couple the capacitor device to sensor signal processing components, where when the switch is latched, the capacitor device is configured to provide power to the sensor signals processing components with the accumulated charge in the capacitor device.

DETAILED DESCRIPTION

Before the present disclosure is described in detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges as also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Figure 1:
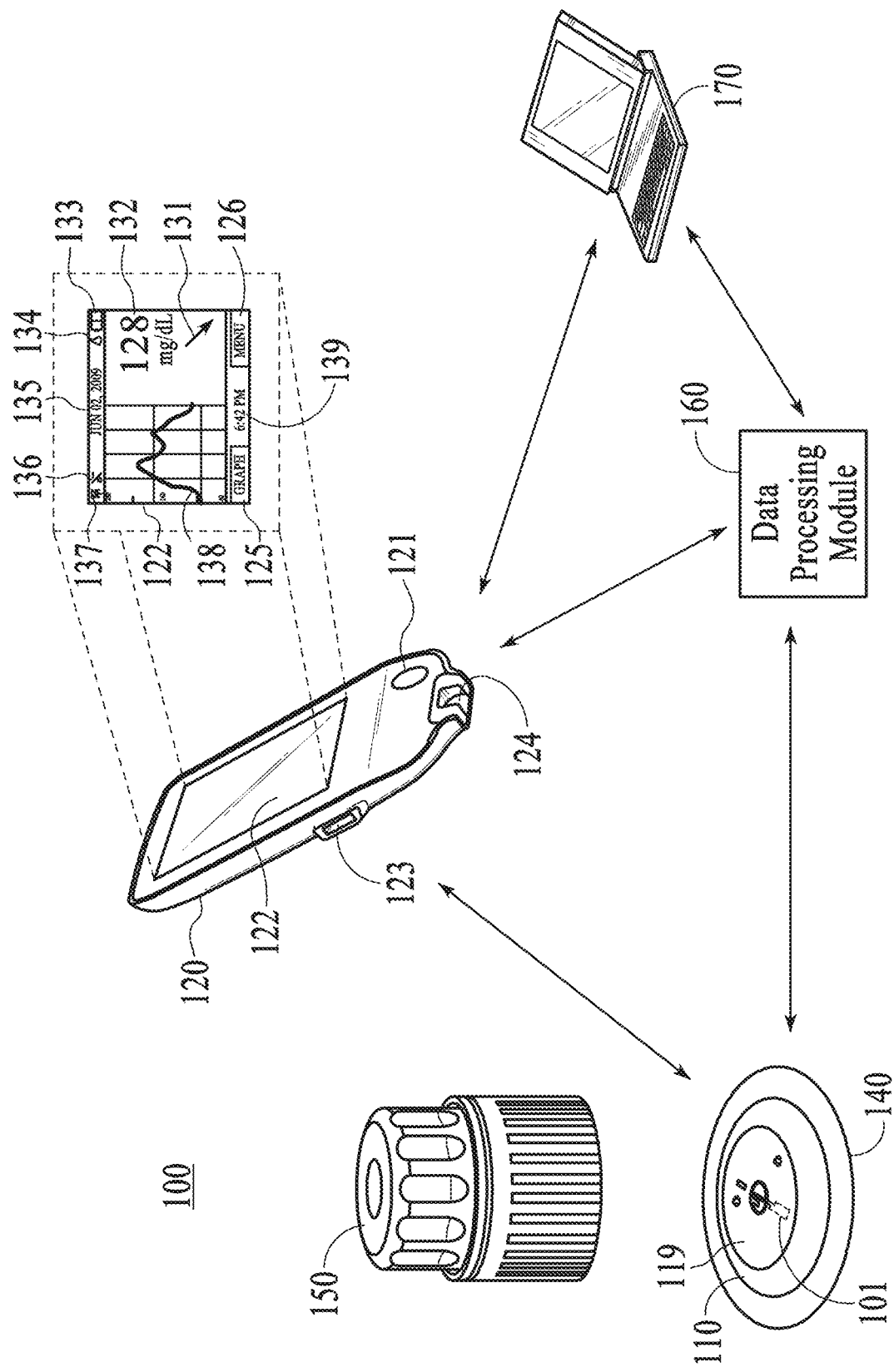
FIG. 1 illustrates an analyte monitoring system for real time analyte (e.g., glucose) measurement, data acquisition and/or processing in accordance with embodiments of the present disclosure.

FIG. 1 shows an exemplary in vivo-based analyte monitoring system 100 in accordance with embodiments of the present disclosure. As shown, in certain embodiments, analyte monitoring system 100 includes on body electronics 110 electrically coupled to in vivo analyte sensor 101 (a proximal portion of which is shown in FIG. 1) and attached to adhesive layer 140 for attachment on a skin surface on the body of a user. On body electronics 110 includes on body housing 119, that defines an interior compartment. Also shown in FIG. 1 is insertion device 150 that, when operated, transcutaneously positions a portion of analyte sensor 101 through a skin surface and in fluid contact with ISF, and positions on body electronics 110 and adhesive layer 140 on a skin surface. In certain embodiments, on body electronics 110, analyte sensor 101 and adhesive layer 140 are sealed within the housing of insertion device 150 before use, and in certain embodiments, adhesive layer 140 is also sealed within the housing or itself provides a terminal seal of the insertion device 150. Devices, systems and methods that may be used with embodiments herein are described, e.g., in U.S. patent application Ser. No. 12/807,278, which published as U.S. Patent Application Publication No. 2011/0213225, the disclosure of which is incorporated herein by reference for all purposes.

Referring back to the FIG. 1, analyte monitoring system 100 includes display device 120 which includes a display 122 to output information to the user, an input component 121 such as a button, actuator, a touch sensitive switch, a capacitive switch, pressure sensitive switch, jog wheel or the like, to input data or command to display device 120 or otherwise control the operation of display device 120. It is noted that some embodiments may include display-less devices or devices without any user interface components. These devices may be functionalized to store data as a data logger and/or provide a conduit to transfer data from on body electronics and/or a display-less device to another device and/or location. Embodiments will be described herein as display devices for exemplary purposes which are in no way intended to limit the embodiments of the present disclosure. It will be apparent that display-less devices may also be used in certain embodiments.

In certain embodiments, on body electronics 110 may be configured to store some or all of the monitored analyte related data received from analyte sensor 101 in a memory during the monitoring time period, and maintain it in memory until the usage period ends. In such embodiments, stored data is retrieved from on body electronics 110 at the conclusion of the monitoring time period, for example, after removing analyte sensor 101 from the user by detaching on body electronics 110 from the skin surface where it was positioned during the monitoring time period. In such data logging configurations, real time monitored analyte level is not communicated to display device 120 during the monitoring period or otherwise transmitted from on body electronics 110, but rather, retrieved from on body electronics 110 after the monitoring time period.

In certain embodiments, input component 121 of display device 120 may include a microphone and display device 120 may include software configured to analyze audio input received from the microphone, such that functions and operation of the display device 120 may be controlled by voice commands. In certain embodiments, an output component of display device 120 includes a speaker for outputting information as audible signals. Similar voice responsive components such as a speaker, microphone and software routines to generate, process and store voice driven signals may be provided to on body electronics 110.

In certain embodiments, display 122 and input component 121 may be integrated into a single component, for example a display that can detect the presence and location of a physical contact touch upon the display such as a touch screen user interface. In such embodiments, the user may control the operation of display device 120 by utilizing a set of pre-programmed motion commands, including, but not limited to, single or double tapping the display, dragging a finger or instrument across the display, motioning multiple fingers or instruments toward one another, motioning multiple fingers or instruments away from one another, etc. In certain embodiments, a display includes a touch screen having areas of pixels with single or dual function capacitive elements that serve as LCD elements and touch sensors.

Display device 120 also includes data communication port 123 for wired data communication with external devices such as remote terminal (personal computer) 170, for example. Example embodiments of the data communication port 123 include USB port, mini USB port, RS-232 port, Ethernet port, Firewire port, or other similar data communication ports configured to connect to the compatible data cables. Display device 120 may also include an integrated in vitro glucose meter, including in vitro test strip port 124 to receive an in vitro glucose test strip for performing in vitro blood glucose measurements.

Referring still to FIG. 1, display 122 in certain embodiments is configured to display a variety of information—some or all of which may be displayed at the same or different time on display 122. In certain embodiments the displayed information is user-selectable so that a user can customize the information shown on a given display screen.

Display 122 may include but is not limited to graphical display 138, for example, providing a graphical output of glucose values over a monitored time period (which may show important markers such as meals, exercise, sleep, heart rate, blood pressure, etc.), numerical display 132, for example, providing monitored glucose values (acquired or received in response to the request for the information), and trend or directional arrow display 131 that indicates a rate of analyte change and/or a rate of the rate of analyte change, e.g., by moving locations on display 122.

As further shown in FIG. 1, display 222 may also include date display 135 providing for example, date information for the user, time of day information display 139 providing time of day information to the user, battery level indicator display 133 which graphically shows the condition of the battery (rechargeable or disposable) of the display device 120, sensor calibration status icon display 134 for example, in monitoring systems that require periodic, routine or a predetermined number of user calibration events, notifying the user that the analyte sensor calibration is necessary, audio/vibratory settings icon display 136 for displaying the status of the audio/vibratory output or alarm state, and wireless connectivity status icon display 137 that provides indication of wireless communication connection with other devices such as on body electronics, data processing module 160, and/or remote terminal 170. As additionally shown in FIG. 1, display 122 may further include simulated touch screen buttons 125, 126 for accessing menus, changing display graph output configurations or otherwise for controlling the operation of display device 120.

Referring back to FIG. 1, in certain embodiments, display 122 of display device 120 may be additionally, or instead of visual display, configured to output alarm notifications such as alarm and/or alert notifications, glucose values etc, which may be audible, tactile, or any combination thereof. In one aspect, the display device 120 may include other output components such as a speaker, vibratory output component and the like to provide audible and/or vibratory output indication to the user in addition to the visual output indication provided on display 122. Further details and other display embodiments can be found in, e.g., U.S. patent application Ser. No. 12/871,901, U.S. provisional application Nos. 61/238,672, 61/247,541, 61/297,625, the disclosures of each of which are incorporated herein by reference for all purposes.

After the positioning of on body electronics 110 on the skin surface and analyte sensor 101 in vivo to establish fluid contact with ISF (or other appropriate body fluid), on body electronics 110 in certain embodiments is configured to wirelessly communicate analyte related data (such as, for example, data corresponding to monitored analyte level and/or monitored temperature data, and/or stored historical analyte related data) when on body electronics 110 receives a command or request signal from display device 120. In certain embodiments, on body electronics 110 may be configured to at least periodically broadcast real time data associated with monitored analyte level which is received by display device 120 when display device 120 is within communication range of the data broadcast from on body electronics 110, i.e., it does not need a command or request from a display device to send information.

For example, display device 120 may be configured to transmit one or more commands to on body electronics 110 to initiate data transfer, and in response, on body electronics 110 may be configured to wirelessly transmit stored analyte related data collected during the monitoring time period to display device 120. Display device 120 may in turn be connected to a remote terminal 170 such as a personal computer and functions as a data conduit to transfer the stored analyte level information from the on body electronics 110 to remote terminal 170. In certain embodiments, the received data from the on body electronics 110 may be stored (permanently or temporarily) in one or more memory of the display device 120. In certain other embodiments, display device 120 is configured as a data conduit to pass the data received from on body electronics 110 to remote terminal 170 that is connected to display device 120.

Referring still to FIG. 1, also shown in analyte monitoring system 100 are data processing module 160 and remote terminal 170. Remote terminal 170 may include a personal computer, a server terminal a laptop computer or other suitable data processing devices including software for data management and analysis and communication with the components in the analyte monitoring system 100. For example, remote terminal 170 may be connected to a local area network (LAN), a wide area network (WAN), or other data network for uni-directional or bi-directional data communication between remote terminal 170 and display device 120 and/or data processing module 160.

Remote terminal 170 in certain embodiments may include one or more computer terminals located at a physician's office or a hospital. For example, remote terminal 170 may be located at a location other than the location of display device 120. Remote terminal 170 and display device 120 could be in different rooms or different buildings. Remote terminal 170 and display device 120 could be at least about one mile apart, e.g., at least about 10 miles apart, e.g., at least about 100 miles apart. For example, remote terminal 170 could be in the same city as display device 120, remote terminal 170 could be in a different city than display device 120, remote terminal 170 could be in the same state as display device 120, remote terminal 170 could be in a different state than display device 120, remote terminal 170 could be in the same country as display device 120, or remote terminal 170 could be in a different country than display device 120, for example.

In certain embodiments, a separate, optional data communication/processing device such as data processing module 160 may be provided in analyte monitoring system 100. Data processing module 160 may include components to communicate using one or more wireless communication protocols such as, for example, but not limited to, infrared (IR) protocol, Bluetooth® protocol, Zigbee® protocol, and 802.11 wireless LAN protocol. Additional description of communication protocols including those based on Bluetooth® protocol and/or Zigbee® protocol can be found in U.S. Patent Publication No. 2006/0193375 incorporated herein by reference for all purposes. Data processing module 160 may further include communication ports, drivers or connectors to establish wired communication with one or more of display device 120, on body electronics 110, or remote terminal 170 including, for example, but not limited to USB connector and/or USB port, Ethernet connector and/or port, FireWire connector and/or port, or RS-232 port and/or connector.

In certain embodiments, data processing module 160 is programmed to transmit a polling or query signal to on body electronics 110 at a predetermined time interval (e.g., once every minute, once every five minutes, or the like), and in response, receive the monitored analyte level information from on body electronics 110. Data processing module 160 stores in its memory the received analyte level information, and/or relays or retransmits the received information to another device such as display device 120. More specifically in certain embodiments, data processing module 160 may be configured as a data relay device to retransmit or pass through the received analyte level data from on body electronics 110 to display device 120 or a remote terminal (for example, over a data network such as a cellular or WiFi data network) or both.

In certain embodiments, on body electronics 110 and data processing module 160 may be positioned on the skin surface of the user within a predetermined distance of each other (for example, about 1-12 inches, or about 1-10 inches, or about 1-7 inches, or about 1-5 inches) such that periodic communication between on body electronics 110 and data processing module 160 is maintained. Alternatively, data processing module 160 may be worn on a belt or clothing item of the user, such that the desired distance for communication between the on body electronics 110 and data processing module 160 for data communication is maintained. In a further aspect, the housing of data processing module 160 may be configured to couple to or engage with on body electronics 110 such that the two devices are combined or integrated as a single assembly and positioned on the skin surface. In further embodiments, data processing module 160 is detachably engaged or connected to on body electronics 110 providing additional modularity such that data processing module 160 may be optionally removed or reattached as desired.

Referring again to FIG. 1, in certain embodiments, data processing module 160 is programmed to transmit a command or signal to on body electronics 110 at a predetermined time interval such as once every minute, or once every 5 minutes or once every 30 minutes or any other suitable or desired programmable time interval to request analyte related data from on body electronics 110. When data processing module 160 receives the requested analyte related data, it stores the received data. In this manner, analyte monitoring system 100 may be configured to receive the continuously monitored analyte related information at the programmed or programmable time interval, which is stored and/or displayed to the user. The stored data in data processing module 160 may be subsequently provided or transmitted to display device 120, remote terminal 170 or the like for subsequent data analysis such as identifying frequency of periods of glycemic level excursions over the monitored time period, or the frequency of the alarm event occurrence during the monitored time period, for example, to improve therapy related decisions. Using this information, the doctor, healthcare provider or the user may adjust or recommend modification to the diet, daily habits and routines such as exercise, and the like.

In another embodiment, data processing module 160 transmits a command or signal to on body electronics 110 to receive the analyte related data in response to a user activation of a switch provided on data processing module 160 or a user initiated command received from display device 120. In further embodiments, data processing module 160 is configured to transmit a command or signal to on body electronics 110 in response to receiving a user initiated command only after a predetermined time interval has elapsed. For example, in certain embodiments, if the user does not initiate communication within a programmed time period, such as, for example about 5 hours from last communication (or 10 hours from the last communication, or 24 hours from the last communication), the data processing module 160 may be programmed to automatically transmit a request command or signal to on body electronics 110. Alternatively, data processing module 160 may be programmed to activate an alarm to notify the user that a predetermined time period of time has elapsed since the last communication between the data processing module 160 and on body electronics 110. In this manner, users or healthcare providers may program or configure data processing module 160 to provide certain compliance with analyte monitoring regimen, so that frequent determination of analyte levels is maintained or performed by the user.

In certain embodiments, when a programmed or programmable alarm condition is detected (for example, a detected glucose level monitored by analyte sensor 101 that is outside a predetermined acceptable range indicating a physiological condition which requires attention or intervention for medical treatment or analysis (for example, a hypoglycemic condition, a hyperglycemic condition, an impending hyperglycemic condition or an impending hypoglycemic condition), the one or more output indications may be generated by the control logic or processor of the on body electronics 110 and output to the user on a user interface of on body electronics 110 so that corrective action may be timely taken. In addition to or alternatively, if display device 120 is within communication range, the output indications or alarm data may be communicated to display device 120 whose processor, upon detection of the alarm data reception, controls the display 122 to output one or more notification.

In certain embodiments, control logic or microprocessors of on body electronics 110 include software programs to determine future or anticipated analyte levels based on information obtained from analyte sensor 101, e.g., the current analyte level, the rate of change of the analyte level, the acceleration of the analyte level change, and/or analyte trend information determined based on stored monitored analyte data providing a historical trend or direction of analyte level fluctuation as function time during monitored time period. Predictive alarm parameters may be programmed or programmable in display device 120, or the on body electronics 110, or both, and output to the user in advance of anticipating the user's analyte level reaching the future level. This provides the user an opportunity to take timely corrective action.

Information, such as variation or fluctuation of the monitored analyte level as a function of time over the monitored time period providing analyte trend information, for example, may be determined by one or more control logic or microprocessors of display device 120, data processing module 160, and/or remote terminal 170, and/or on body electronics 110. Such information may be displayed as, for example, a graph (such as a line graph) to indicate to the user the current and/or historical and/or and predicted future analyte levels as measured and predicted by the analyte monitoring system 100. Such information may also be displayed as directional arrows (for example, see trend or directional arrow display 131) or other icon(s), e.g., the position of which on the screen relative to a reference point indicated whether the analyte level is increasing or decreasing as well as the acceleration or deceleration of the increase or decrease in analyte level. This information may be utilized by the user to determine any necessary corrective actions to ensure the analyte level remains within an acceptable and/or clinically safe range. Other visual indicators, including colors, flashing, fading, etc., as well as audio indicators including a change in pitch, volume, or tone of an audio output and/or vibratory or other tactile indicators may also be incorporated into the display of trend data as means of notifying the user of the current level and/or direction and/or rate of change of the monitored analyte level. For example, based on a determined rate of glucose change, programmed clinically significant glucose threshold levels (e.g., hyperglycemic and/or hypoglycemic levels), and current analyte level derived by an in vivo analyte sensor, the system 100 may include an algorithm stored on computer readable medium to determine the time it will take to reach a clinically significant level and will output notification in advance of reaching the clinically significant level, e.g., 30 minutes before a clinically significant level is anticipated, and/or 20 minutes, and/or 10 minutes, and/or 5 minutes, and/or 3 minutes, and/or 1 minute, and so on, with outputs increasing in intensity or the like.

Referring again back to FIG. 1, in certain embodiments, software algorithm(s) for execution by data processing module 160 may be stored in an external memory device such as an SD card, micro-SD card, compact flash card, XD card, Memory Stick card, Memory Stick Duo card, or USB memory stick/device including executable programs stored in such devices for execution upon connection to the respective one or more of the on body electronics 110, remote terminal 170 or display device 120. In a further aspect, software algorithms for execution by data processing module 160 may be provided to a communication device such as a mobile telephone including, for example, WiFi or Internet enabled smart phones or personal digital assistants (PDAs) as a downloadable application for execution by the downloading communication device.

Examples of smart phones include Windows®, Android™, iPhone® operating system, Palm® WebOS™, Blackberry® operating system, or Symbian® operating system based mobile telephones with data network connectivity functionality for data communication over an internet connection and/or a local area network (LAN). PDAs as described above include, for example, portable electronic devices including one or more microprocessors and data communication capability with a user interface (e.g., display/output unit and/or input unit, and configured for performing data processing, data upload/download over the internet, for example. In such embodiments, remote terminal 170 may be configured to provide the executable application software to the one or more of the communication devices described above when communication between the remote terminal 170 and the devices are established.

In still further embodiments, executable software applications may be provided over-the-air (OTA) as an OTA download such that wired connection to remote terminal 170 is not necessary. For example, executable applications may be automatically downloaded as software download to the communication device, and depending upon the configuration of the communication device, installed on the device for use automatically, or based on user confirmation or acknowledgement on the communication device to execute the installation of the application. The OTA download and installation of software may include software applications and/or routines that are updates or upgrades to the existing functions or features of data processing module 160 and/or display device 120.

Referring back to remote terminal 170 of FIG. 1, in certain embodiments, new software and/or software updates such as software patches or fixes, firmware updates or software driver upgrades, among others, for display device 120 and/or on body electronics 110 and/or data processing module 160 may be provided by remote terminal 170 when communication between the remote terminal 170 and display device 120 and/or data processing module 160 is established. For example, software upgrades, executable programming changes or modification for on body electronics 110 may be received from remote terminal 170 by one or more of display device 120 or data processing module 160, and thereafter, provided to on body electronics 110 to update its software or programmable functions. For example, in certain embodiments, software received and installed in on body electronics 110 may include software bug fixes, modification to the previously stalled software parameters (modification to analyte related data storage time interval, resetting or adjusting time base or information of on body electronics 110, modification to the transmitted data type, data transmission sequence, or data storage time period, among others).

Further embodiments, details and configurations of the analyte monitoring system can be found in U.S. patent application Ser. No. 12/807,278, which published as U.S. Patent Application Publication No. 2011/0213225, the disclosure of which is incorporated herein by reference for all purposes.

Figure 2:
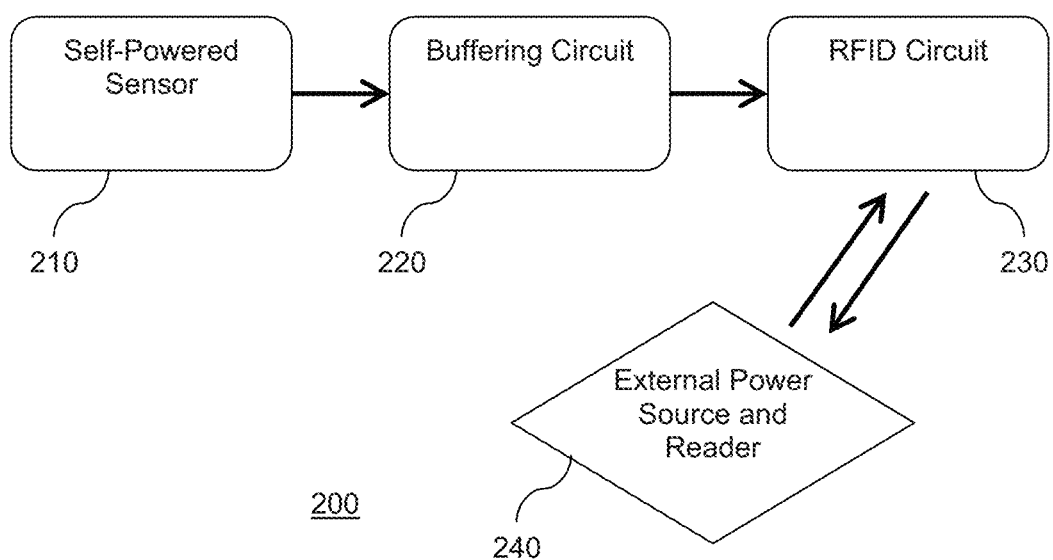
FIG. 2 is a block diagram of an analyte monitoring system including a self-powered analyte sensor and RFID data communication module in accordance with embodiments of the present disclosure.

FIG. 2 is a block diagram of an analyte monitoring system including a self-powered analyte sensor and RFID data communication module in accordance with one embodiment of the present disclosure. As shown in FIG. 2, in certain embodiments, the analyte monitoring system 200 includes self-powered sensor 210 operatively coupled to buffering circuit 220 that is further provided in signal communication with RFID circuit 230. The self-powered sensor 210, the buffering circuit 220 and the RFID circuit 230 in certain embodiments may be provided in a single on body sensor electronics housing, with a portion of the self-powered sensor 210 positioned under the skin surface of a user and in fluid contact with interstitial fluid. The single on body sensor electronics housing in certain embodiments is a waterproof housing. Referring back to FIG. 2, also shown is an external power source and Reader device ("reader") 240 which in certain embodiments, includes an RFID reader that is capable of radiating an RF field, and when in proximity to an RFID device, receives data communication back from the RFID device using the RF field.

In certain embodiments, self-powered sensor 210 includes at least a working electrode and a counter electrode and power is generated as a result of the oxidation reaction between the working and counter electrodes. Additional details on the structure, operation and configurations of self-powered sensor 210 can be found in U.S. patent application Ser. No. 12/393,921, published as US 2010/0213057, U.S. patent application Ser. No. 13/087,190 published as US 2011/0257495, and U.S. patent application Ser. No. 13/299,119 published as US 2012-0157801, the disclosures of each of which are incorporated herein by reference for all purposes.

For example, in certain embodiments, self-powered sensor 210 generates an average current of about 10 nA to about 100 nA with an average voltage of about 100 mV to about 300 mV, resulting in an average power output of about 1 nW to 30 nW. It is to be understood that the current, voltage and power ranges described herein are representative and the disclosure is not limited to the ranges mentioned herein. In certain embodiments, a low current may be desired for the electrode pair utilized for measuring analyte levels. In such embodiments, a second working electrode and counter electrode pair may be included in the self-powered sensor 210, and be configured for higher current output for power generation.

Referring to FIG. 2, in certain embodiments, the self-powered sensor 210 operates continuously, without the use of an external power source, to generate current signals that are proportional to the analyte concentration in the bodily fluid that the self-powered sensor 210 is placed in contact therewith. The RFID circuit 230 and the buffering circuit 220, in certain embodiments, remain dormant or in an inactive or nonoperational state while the self-powered sensor 210 is generating the current signals. In certain embodiments, when Reader 240 is positioned in close proximity to the RFID circuit 230 of the on body sensor electronics such that the RFID circuit 230 is within the RF field radiated from the Reader 240, the RFID circuit is configured to query the self-powered sensor 210 through the buffering circuit 220 to receive the measured sensor current signal, and sends or returns the measured sensor current signal (received from the self-powered sensor 210 via the buffering circuit 220) to the Reader 240. As described further below and also shown in FIG. 6, self-powered sensor 210, in certain embodiments, is connected to an R/C (resistor/capacitor) load providing a return current path for self-powered sensor 210. Measured voltage across the R/C load generated when the generated current flows through the R/C load, provides one or more signals which is passed (through the buffering circuit 220) to the RFID circuit 230. In certain embodiments, the signals communicated by the RFID circuit 230 in response to the query from the Reader 240 include analog signals generated by the self-powered sensor corresponding to the monitored analyte levels digitized for data transmission, measured temperature data, and calibration code information.

Figure 3:
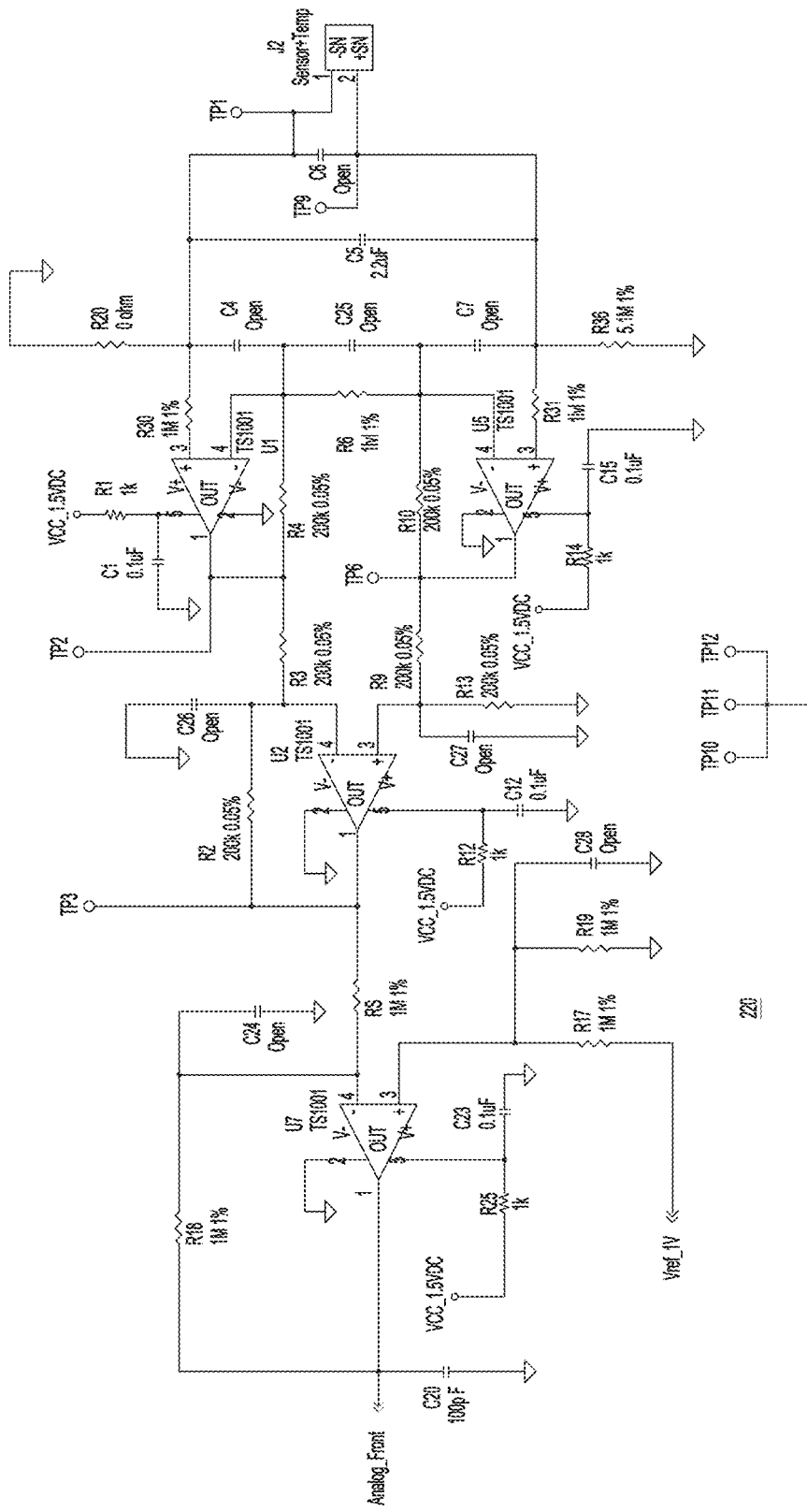
FIG. 3 illustrates the buffering circuit of the analyte monitoring system shown in FIG. 2 in accordance with embodiments of the present disclosure.

FIG. 3 illustrates the buffering circuit 220 of the analyte monitoring system 200 shown in FIG. 2 in accordance with embodiments of the present disclosure. As shown, buffering circuit 220 shown in FIG. 3 is an instrumentation operational amplifier (OPA) used to isolate the self-powered sensor 210 (FIG. 2) from the RFID circuit 230 (FIG. 2). The input buffers may include one or more operational amplifiers with high impedance to isolate the signals from the self-powered sensor 210 from the RFID circuit 230, and maintain the accuracy of the monitored analyte level readings generated by the self-powered sensor 210. In certain embodiments the buffering circuit 220 is a close to unity gain amplifier and passes the analog voltage signals to RFID circuit 230.

Figure 4:
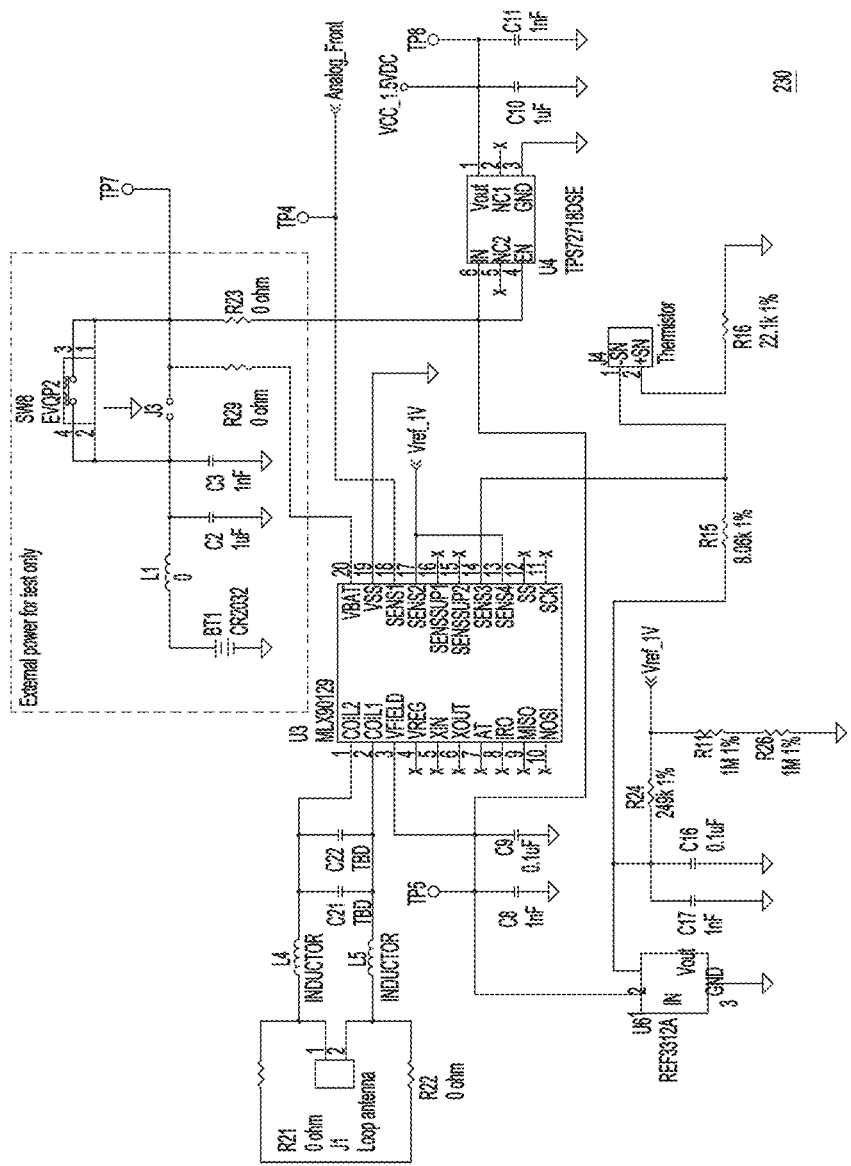
FIG. 4 illustrates the RFID circuit of the analyte monitoring system shown in FIG. 2 in accordance with embodiments of the present disclosure.

FIG. 4 illustrates the RFID circuit 230 of the analyte monitoring system shown in FIG. 2 in accordance with embodiments of the present disclosure. Referring to FIG. 4, the RFID circuit 230 in certain embodiments includes an antenna and an RFID chip. The RFID circuit 230 also includes a voltage reference used to raise the bias potential for the buffering circuit 220 and for the analog front end circuitry of the RFID chip, as well as a precision voltage regulator. In operation, when the Reader 240 is positioned in close proximity to the RFID circuit 230, the RF field radiated from the Reader 240 provides the necessary power to operate the buffering circuit 220 and the RFID circuit 230. Further, signals received from the Reader 240 initialize the RFID circuit 230 by resetting the digital circuits and setting the digital bits of the memory and registers of the RFID circuit 230. RFID query commands are sent to the RFID circuit 230, and in response, the RFID circuit 230 transmits the digitized signals associated with the monitored analyte level to the Reader 240.

Figure 5:
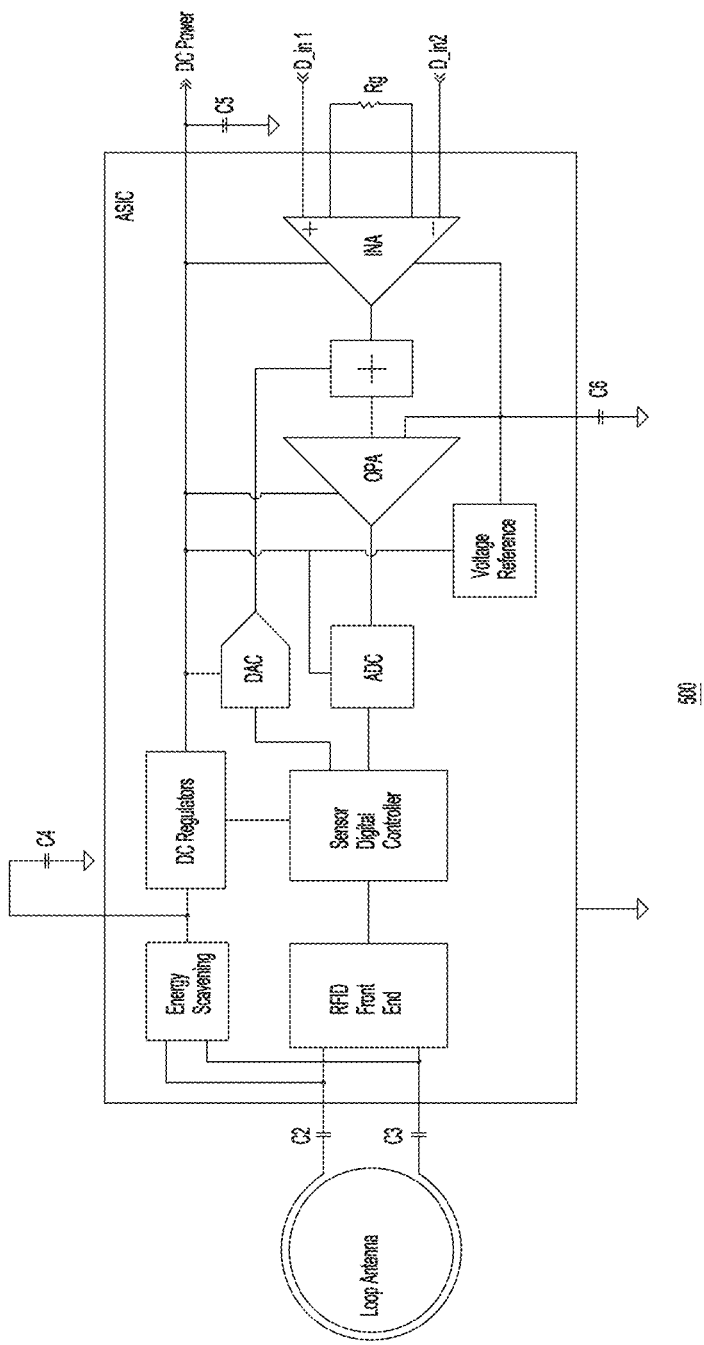
FIG. 5 illustrates an application specific integrated circuit (ASIC) which incorporates the RFID functionality of FIG. 4 in a single circuit in accordance with embodiments of the present disclosure.

FIG. 5 illustrates an application specific integrated circuit (ASIC) which incorporates the function of the RFID circuit shown in FIG. 4 and the function of the buffering circuit 220 shown in FIG. 3 in a single ASIC configuration 500. In certain embodiments, ASIC 500 includes an ISO 15693 RFID front-end circuitry, a magnetic field energy saving circuit, DC power management (regulators), sensor digital control, analog to digital and digital to analog converters and an analog front end circuitry. An IOS 15963 RFID front-end circuitry provides wireless access for Reader 240 to acquire digitized data from the ASIC 500. A magnetic field energy saving circuit converts the magnetic field energy received from the Reader 240 to DC power to supply power to the ASIC 500 when Reader 240 is in proximity. A DC power management circuit utilizes the DC power generated at the magnetic field energy saving circuit to provide stable and filtered DC power for the ASIC 500. A sensor digital control circuit initializes and programs ASIC 500, controls the analog to digital processing and analog front end gain, and provides digitized data to the RFID front-end circuitry. An analog to digital converter (ADC) converts the analog signals to a corresponding digital signal for the RFID front-end backscatter modulation and a digital to analog converter (DAC) is used to compensate error due to analog front end offset voltage. An analog front end circuitry amplifies the analog signals received from self-powered sensor 210 for ADC conversion.

Figure 6:
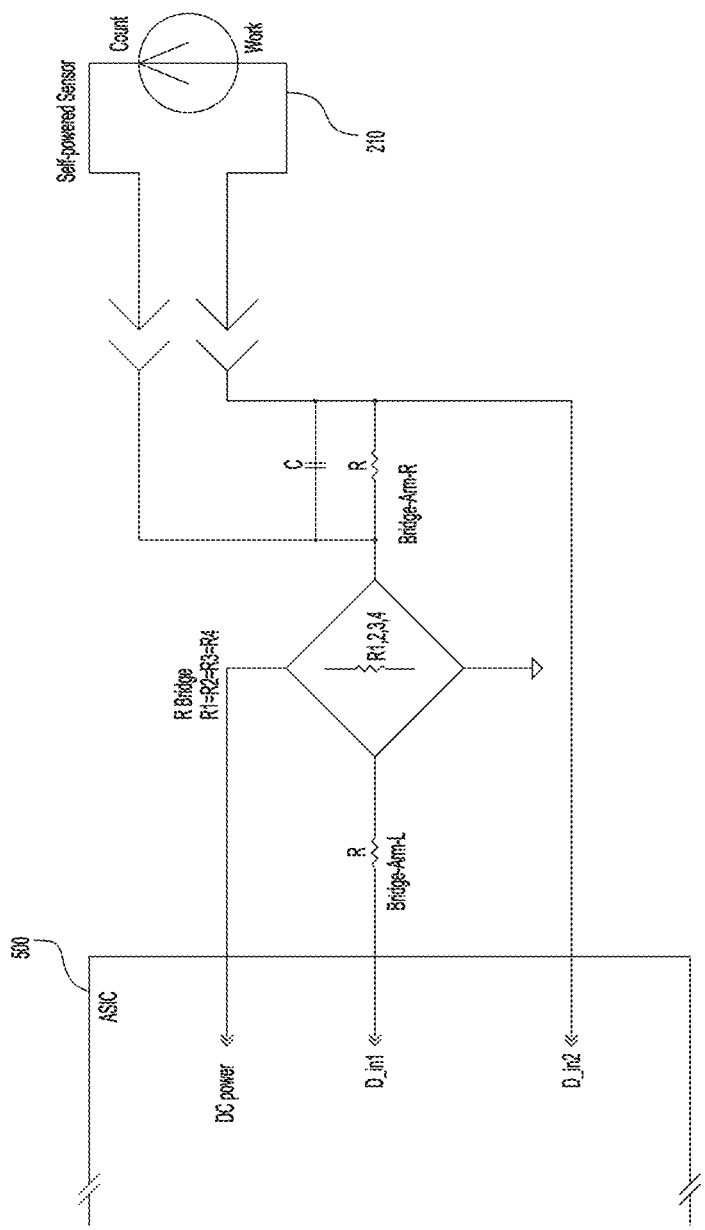
FIG. 6 illustrates a sensor interface resistor capacitor (RC) network to interface between the self-powered sensor and the ASIC shown in FIG. 5 that incorporates the functions of the buffering circuit and the RFID circuit (shown in FIGS. 2-4) in accordance with certain embodiments of the present disclosure.

FIG. 6 illustrates a sensor interface resistor capacitor (RC) network to interface between the self-powered sensor 210 and the ASIC shown in FIG. 5 that incorporates the functions of the buffering circuit 220 and the RFID circuit 230 (shown in FIGS. 2-4) in accordance with certain embodiments of the present disclosure. In particular, in certain embodiments, a resistor bridge circuit with two resistor arms 600 is provided between the ASIC 500 of FIG. 5 with the self-powered sensor 210. The resistor bridge circuit provides bias for both inputs of the ASIC 500 and allows for maintenance of accuracy of the analyte measurement signal even at low current levels. The voltage across the ASIC input terminals D_in1, D_in2 is the sensor voltage across resistor R to be proportional to the sensor current received from the self-powered sensor 210. The bias voltage provided to both input arms of the ASIC 500 maintains a constant differential voltage for a given resistance. An R/C sensor load is connected in parallel with self-powered sensor 210 and in series between the bridge circuit and one input of the ASIC 500. The voltage variations across the R/C load applies to the differential voltage between the two inputs of the ASIC 500 and corresponds to the sensor measurement signal received by the ASIC 500. The resistor bridge further provides a compensation voltage to cancel any leakage current effect when there is bias current flowing out or in through the inputs of the ASIC 500.

Figure 7:
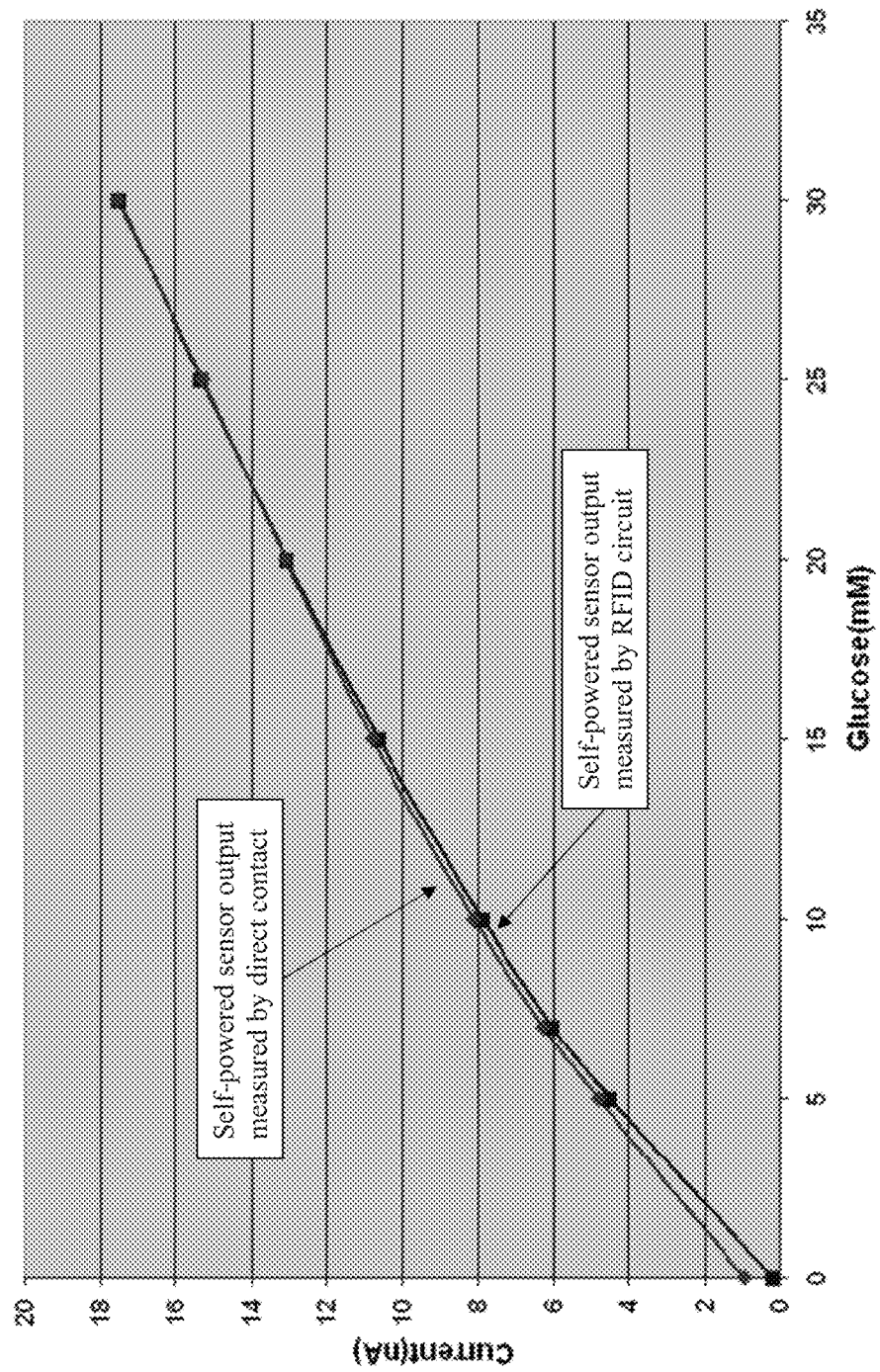
FIG. 7 is a graph comparing the results of a first calibration test measured by directly contacting the intervening resistor with a precision voltmeter, and a second calibration test obtained by remotely powering the RFID and buffering circuits through an external power source in accordance with embodiments of the present disclosure.

FIG. 7 is a graph comparing the results of a first calibration test measured by directly contacting the intervening resistor with a precision voltmeter, and a second calibration test obtained by remotely powering the RFID and buffering circuits through an external power source. Referring to FIG. 7, the test included a self-powered sensor with a glucose oxide anode and a carbon cathode and an intervening 5MΩ resistor. The self-powered sensor was immersed in a buffer solution and glucose aliquots were added. The test was repeated (1) for a directly contacted intervening resistor and (2) by remotely powering RFID and buffering circuits. Self-powered sensor and corresponding circuitry configurations were tested to determine the accuracy and potential for signal loss by utilizing RFID communication versus direct contact communication. The test configurations had an external power source attached thereto to test the calibration of the test configurations.

Figure 8:
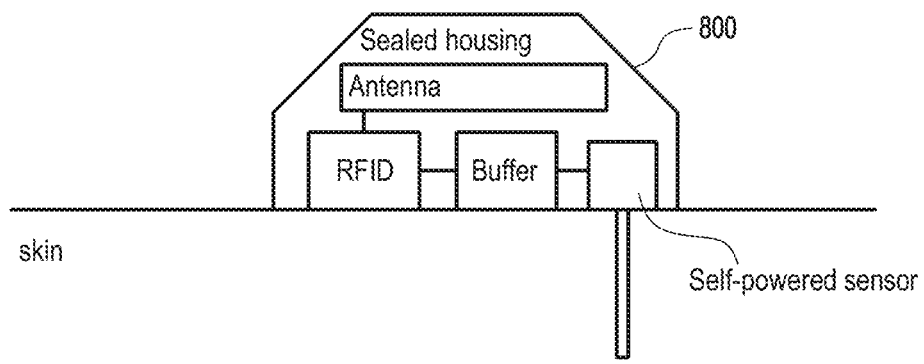
FIG. 8 illustrates a sealed, waterproof on body sensor electronics housing including the self-powered sensor, the buffering circuit and the RFID circuit and antenna described above in conjunction with FIGS. 2-5 in certain embodiments of the present disclosure.

FIG. 8 illustrates a sealed, waterproof on body sensor electronics housing 800 including the self-powered sensor, the buffering circuit and the RFID circuit and antenna described above in conjunction with FIGS. 2-5 in certain embodiments of the present disclosure. Referring to FIG. 8, a portion of the self-powered sensor extends from the sealed on body sensor electronics housing, and upon positioning of the sensor electronics housing, the sensor portion that extends from the housing is positioned under the skin surface and in contact with the interstitial fluid. In this manner, in certain embodiments, the sealed sensor electronics housing including sensor electronics such as the buffering circuit and the RFID circuit can be sterilized with gamma ray or e-bam radiation as the housing does not include a memory device that may be susceptible to such sterilization.

Figure 9:
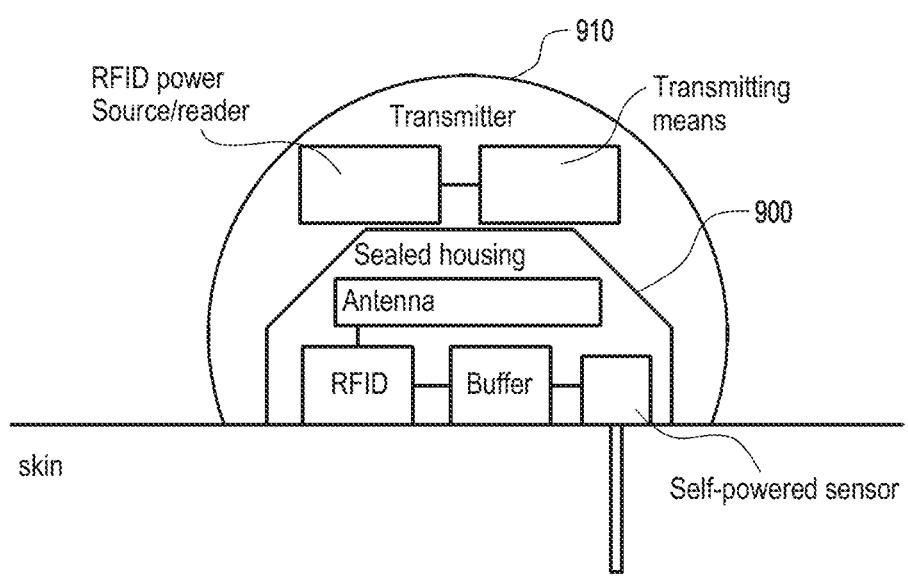
FIG. 9 illustrates a sealed, waterproof on body sensor electronics housing including the self-powered sensor, the buffering circuit and the RFID circuit and antenna described above in conjunction with FIGS. 2-5, and further including a data communication component coupled to the on body sensor electronics housing in certain embodiments of the present disclosure.

FIG. 9 illustrates a sealed, waterproof on body sensor electronics housing 900 including the self-powered sensor, the buffering circuit and the RFID circuit and antenna described above in conjunction with FIGS. 2-5, and further including a data communication device 910 coupled to the on body sensor electronics housing in certain embodiments of the present disclosure. Referring to FIG. 9, the sealed on-body sensor electronics housing may be coupled with a data communication device that may be reversibly snapped onto the sealed sensor electronics housing, or alternatively detachably attached with mechanical features such as grooves, latches, locks arms and the like.

The data communication device in certain embodiments includes RFID power source and reader device, and alternatively, also include an RF data communication module. In certain embodiments, the RFID power source and reader device may be programmed or is programmable to query the sensor electronics to retrieve sensor signals corresponding to monitored analyte level at a predetermined or programmed or programmable time interval, which, upon receipt, may also retransmit or communicate the received sensor signals to a remote location, for example, using the RF data communication module within the data communication device. In certain embodiments, alarms and projected measurement values can be determined based upon the stored analyte level measurements. In certain embodiments, the data communication device may be powered separately and remotely for extended life.

In the manner described above, self-powered sensor is configured to operate with a buffering circuit and RFID circuit, where upon receipt of a query signal from the Reader device (that provides RF field), the RFID circuit and the buffer circuit transition into active operational mode to retrieve the sensor signal from the self-powered sensor and to provide data related to monitored analyte level corresponding to the retrieved sensor signal to the Reader device. Further, in certain embodiments of the present disclosure, self-powered sensor and electronics assembly are provided in a single waterproof housing that meets or exceeds IPX-7 level, which can be sterilized using a single sterilization technique without potential damage to the assembly since the assembly does not include a memory device that may be susceptible to the suitable gamma ray or e-beam sterilization.

Figure 10:
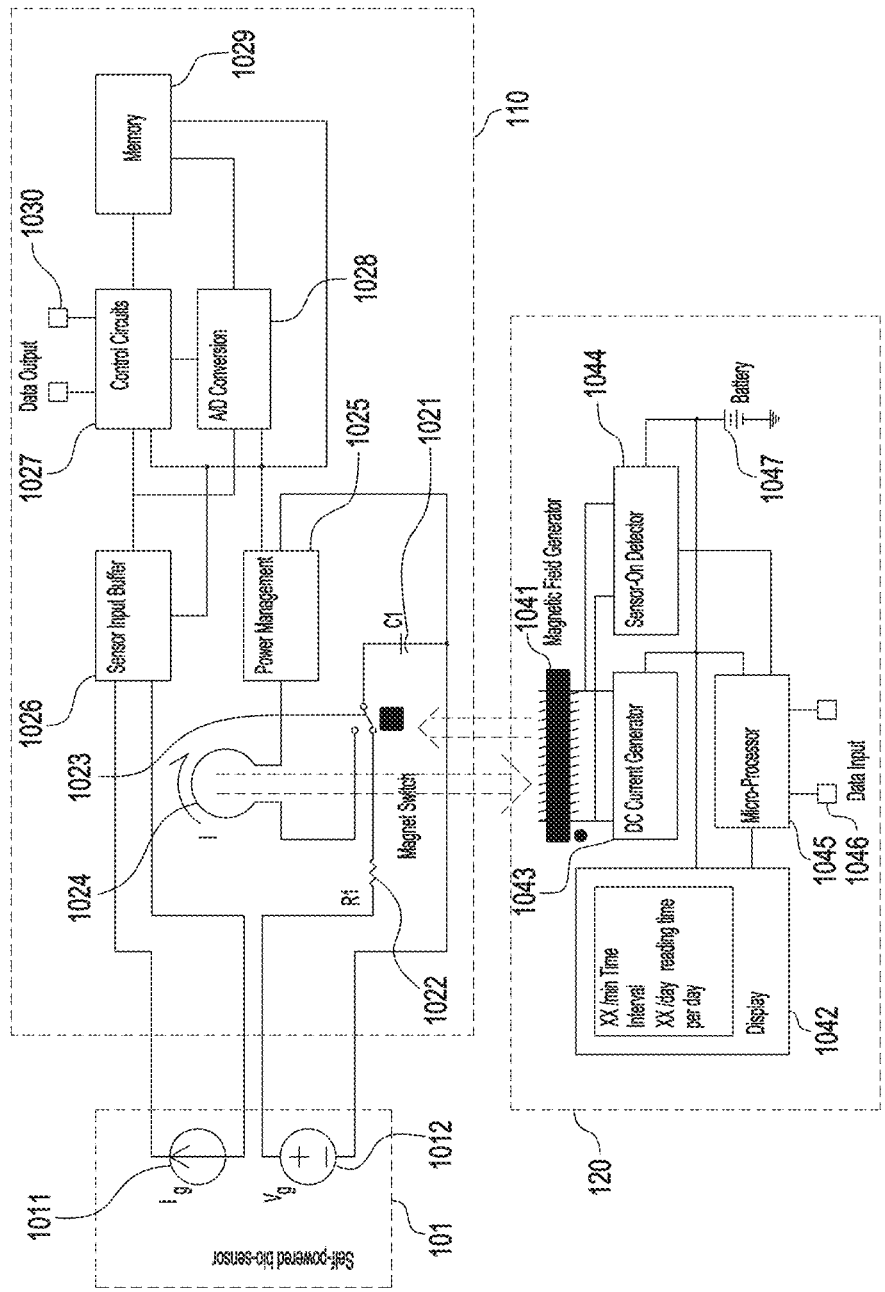
FIG. 10 illustrates an analyte monitoring system including a self-powered analyte sensor, on body sensor electronics and reader device in accordance with embodiments of the present disclosure.

FIG. 10 illustrates an analyte monitoring system including a self-powered analyte sensor, on body sensor electronics and reader device in accordance with embodiments of the present disclosure. Referring to FIG. 10, sensor electronics 110 includes a capacitor 1021 and resistor 1022, wherein the voltage 1012 generated by the analyte sensor runs through the resistor 1022 to charge capacitor 1021 which stores charge resulting in the current signals generated by the self-powered analyte sensor 101. Capacitor 1021 is sized to store sufficient charge to power sensor electronics 110 for a time period sufficient to measure and store analyte values monitored by the analyte sensor, without the use of any external power supply such as a battery. In certain embodiments, the sensor electronics 110 includes a switch 1023.

Switch 1023, when activated, switches or latches the power loop from charging the capacitor 1021 via the self-powered analyte sensor 101, to a circuit loop whereby the capacitor 1021 discharges to flow through a power management module 1025, which in certain embodiments, includes a voltage multiplier to increase the voltage from capacitor 1021 to a sufficiently high voltage for operation of sensor electronics 110 to read and store a measured analyte value. For example, in certain embodiments, for operation of the sensor electronics 110, approximately 500 mV is used as the minimum charging input voltage from the sensor, and the 500 mV is doubled in the power management module 1025 to power on sensor electronics circuits.

Sensor electronics 110 for measurement, processing and storage of signals corresponding to monitored analyte level includes power management module 1025, a sensor input buffer 1026, control circuits 1027, an analog-to-digital (A/D) converter 1028, a memory 1029 and a data output module 1030. In certain embodiments, power management module 1025 is configured to multiply, regulate and detect the charge stored or accumulated in capacitor 1021 before powering the entire sensor circuitry of sensor electronics 110. Sensor input buffer 1026 includes an instrumental operational amplifier of high impedance and a resistor bridge network, which acts as a buffer between analyte sensor 101 and A/D converter 1028. The resistor bridge provides reference voltage (Vcc/2) for the inputs of the instrumental operation amplifier. One of the arms of the resistor bridge is connected to input of the instrumental operation amplifier through a sensor load R/C circuit.

Sensor input buffer 1026 is used due to the low analyte current level generated at analyte sensor corresponding to the measurement of an analyte level, to minimize the impact on the analyte current measurement. Since the input impedance of the instrumental operation amplifier is very high, the sensor current will not flow (through) in or out of the inputs of the instrumental amplifier when the sensor is connected. Thus, the sensor current measurement will not be affected by the external circuits connected to the sensor.

A/D converter 1028 converts the analog analyte current signals from analyte sensor 101 via the signal input buffer 1026, to a digital value to be stored on memory 1029. Data output module 1030 is utilized to transmit, either via direct contact or wirelessly, data stored on memory 1029 to display device 120 or other electronic device with a compatible physical and/or wireless input port.

Control circuits 1027 control the signal flow among the various sensor electronics 110 components, including the sensor input buffer 1026, A/D converter 1028, memory 1029, and data output module 1030. In certain embodiments, control circuit 1027 is configured to initialize digital settings and start measurement, to control the gain of the instrumental operation amplifier to provide amplified analog signal for A/D converter 1028, and to store the converted digital data into memory 1029 and upload the data from the memory 1029 to display device 120.

In certain embodiments, sensor electronics 110 uses approximately 100 µW for approximately 100 ms (approximately 10 microjoules) to measure and store an analyte measurement. Self-powered analyte sensor 101, in certain embodiments, generates approximately 25 nW, which would take approximately 400 s (7 minutes) to accumulate the 10 microjoules necessary to measure and store the analyte measurement. In such embodiments, the analyte monitoring system 100 can be configured to measure and store an analyte measurement at least every 7 minutes without the need of a battery or other external power source.

Still referring to FIG. 10, and as illustrated in FIG. 1, analyte monitoring system 100 includes display device 120. Display device 120 may be configured to transmit a signal to the sensor electronics 110 to activate switch 1023 to begin measurement and storage of an analyte value. In certain embodiments, display device 120 may include a magnetic field generator 1041, and switch 1023 may be a magnetic switch, where upon activation of the magnetic field generator 1041, the magnetic switch switches operation of sensor electronics 110 from charging the capacitor 1021 to measurement and storage of an analyte value. Switch 1023 is connected to sensor 101 through R1, which limits the charging current, before magnetic field presents next to it. In such way, the sensor will charge the capacitor 1021 in most time. Since the sensor can only generate ultra-low current, it will take a long time to fully charge the capacitor 1021. The magnetic field generator 1041 in certain embodiments includes conductive wire loops and soft iron. The magnetic field is generated with a current from a direct current (DC) current source 1043 flowing through the conductive wire loops, while the soft iron enhances the magnetic field.

In further embodiments, sensor electronics 110 also includes a wire loop 1024, which, upon detection of current flowing through the wire loop 1024 due to magnetic switching of switch 1023, generates a magnetic pulse signal. The magnetic pulse signal is detected by the display device 120 to confirm that the magnetic actuation of the switch 1023 and confirm the magnetic field generator 1041 signal was received at the sensor electronics 110. When switch 1023 is connected to wire loop 1024, the initial pulse signal in the form of the magnetic field will disturb the magnetic field produced by the magnetic field generator 1041. The magnetic field will cause current change across the conductive loop wire 1024. The sensor-on detector 1044 will detect the current changes to confirm the switch 1023 status change.

In certain embodiments, the magnetic pulse signal is detected by a sensor-on detector 1044 of the display device 120. The display device 1042 displays how many times the user activates the sensor electronics 110, and the day and time information from the last activation time. Since the capacitor 1021 charging will take a certain amount of time, activation spaced too close together will not provide sufficient time for capacitor 1021 to be fully charged. In certain embodiments, microprocessor 1045 is configured to turn on DC current generator 1043, detect sensor-on detector 1044 status, monitor battery voltage, download the data from sensor electronics 110 and operate the display device 1042. Display device 120 may further include a display 1042, microprocessor 1045, data input module 1046 and battery 1047.

Figure 11:
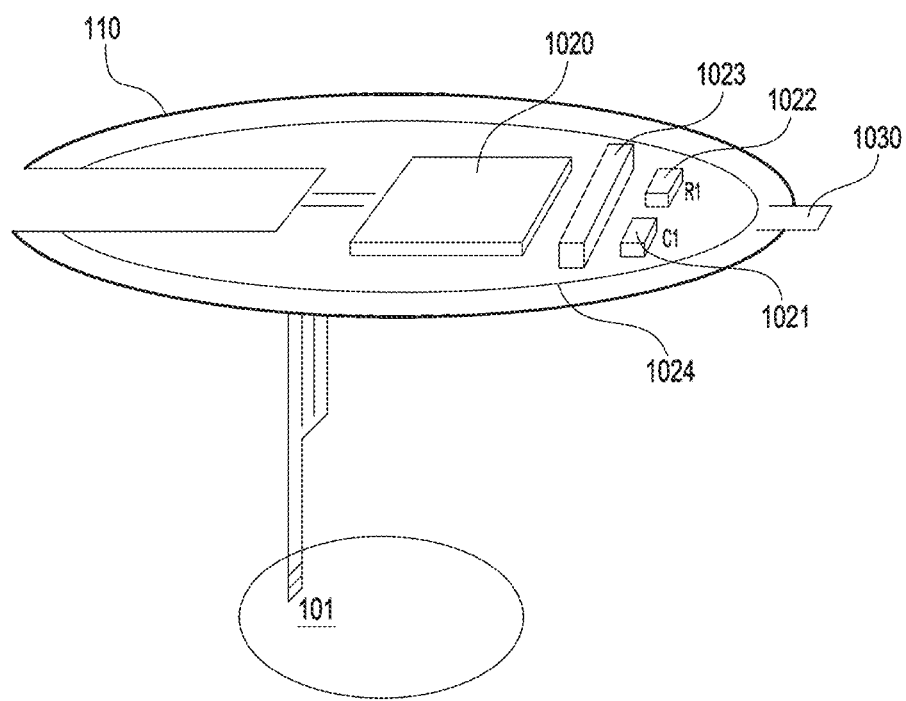
FIG. 11 illustrates an embodiment of the sensor electronics and self-powered analyte sensor of FIG. 10 in accordance with embodiments of the present disclosure.

FIG. 11 illustrates an embodiment of the sensor electronics 110 and self-powered analyte sensor 101 of FIG. 10. Referring to FIG. 11, self-powered analyte sensor 101 and sensor electronics 110 including wire loop 1024, magnetic switch 1023, capacitor 1021, resistor 1022, a physical data output 1030 and electronics 1020 including power management module 1025, sensor input buffer 1026, control circuits 1027, A/D converter 1028 and memory 1029 are integrated into a single device. In other embodiments, analyte sensor 101 is separate from the sensor electronics 110 and is physically and/or electrically coupled with the sensor electronics 110 before, during or after transcutaneous insertion through the skin surface.

In other embodiments, sensor electronics 110 components are located on two or more separate devices. For example, in certain embodiments, a first device may include analyte sensor 101 integrated with sensor electronics 110 components including wire loop 1024, switch 1023, capacitor 1021, resistor 1022 and physical data output 1030, while a second device which is configured to be physically coupled to the first device, includes electronics 1020 including power management module 1025, sensor input buffer, 1026, control circuits 1027, A/D converter 1028 and memory 1029. The second device may include a physical data input that is physically coupled with physical data output 1030 to facilitate transfer of data and signals between the first and second device. Further, second device may further include an output, either physical contacts or wireless communication, such as radio frequency (RF), which communicates with display device 120.

Figure 12:
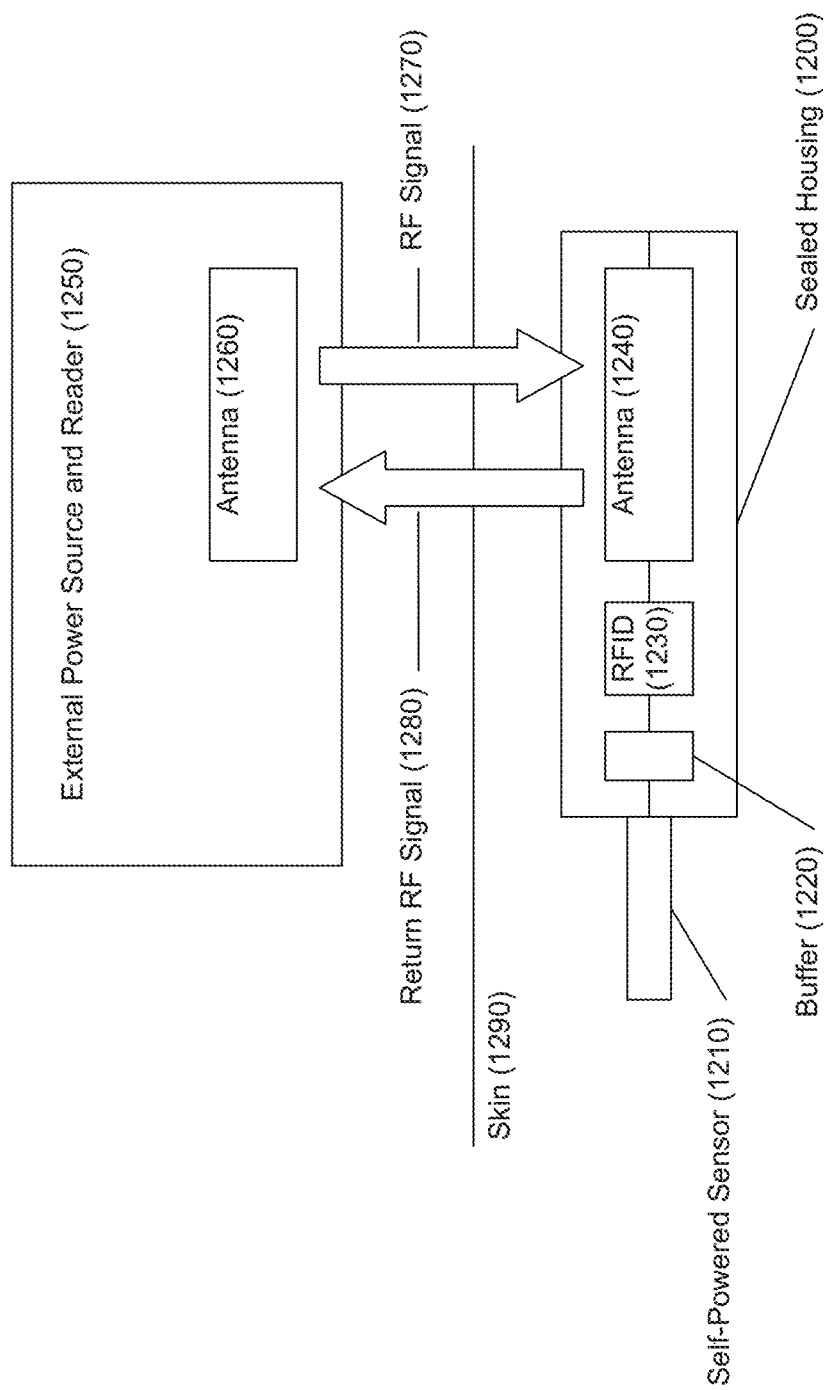
FIG. 12 illustrates a fully implantable self-powered sensor and sensor electronics in accordance with certain embodiments of the present disclosure.

FIG. 12 illustrates a fully implantable self-powered sensor and sensor electronics in accordance with certain embodiments of the present disclosure. In certain embodiments, self-powered sensor 1210 and sensor electronics including buffer circuit 1220, RFID circuit 1230 and antenna 1240 are provided in a sealed housing 1200 and configured to be fully implantable under skin surface 1290. As described in detail above, self-powered sensor 1210 and sensor electronics are configured to be externally powered via magnetic field provided by Reader 1250. In this manner, in certain embodiments, self-powered sensor 1210 and sensor electronics to be configured for long-term implantation beneath a skin surface 1290 of a user. In certain embodiments, implantable self-powered sensor 1210 receives an RF signal 1270 request from Reader 1250, and transmits a return RF signal 1280 for receipt at the Reader antenna 1260. Return RF signal 1280 includes the sensor data measured by the self-powered sensor 1210. In certain embodiments, sensor electronics may be a single ASIC within the sealed housing 1200.

Figure 13:
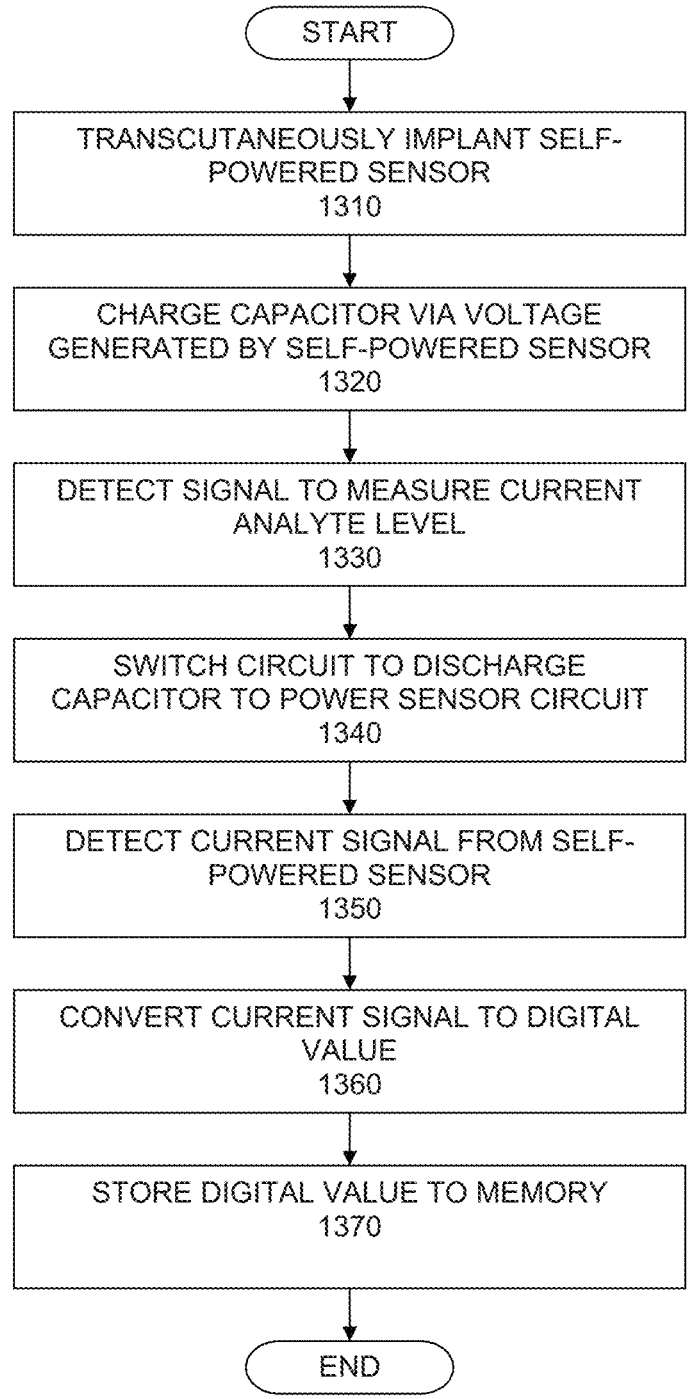
FIG. 13 is a flow chart illustrating a method of monitoring a level of an analyte of a user in accordance with embodiments of the present disclosure.

FIG. 13 is a flow chart illustrating analyte monitoring in certain embodiments of the present disclosure. Referring to FIG. 13, after transcutaneous positioning of a self-powered analyte sensor (1310), the oxidation reaction between the working and counter electrodes of the self-powered analyte sensor generates current signals that is then used by the sensor electronics to charge a capacitor for powering the sensor electronics (1320). Referring back to FIG. 13, periodically, the sensor electronics receive a signal to measure a current analyte level (1330). In certain embodiments, the signal is generated automatically at periodic intervals, and in other embodiments, the signal is generated based on a command from a display device. Upon receipt of the signal, a switch in the sensor electronics is activated, which switches the flow of power between the self-powered sensor and capacitor to discharge the capacitor to power the sensor electronics (1340). Upon activation of the sensor electronics, the current signal measured at the self-powered sensor representative of a current analyte level is detected by the sensor electronics (1350). The measured current signal of the self-powered sensor is converted to a digital value (1360) by the A/D converter of the sensor electronics. The digital value is then stored in memory (1370) for later retrieval or transmission to a display device.

Figure 14:
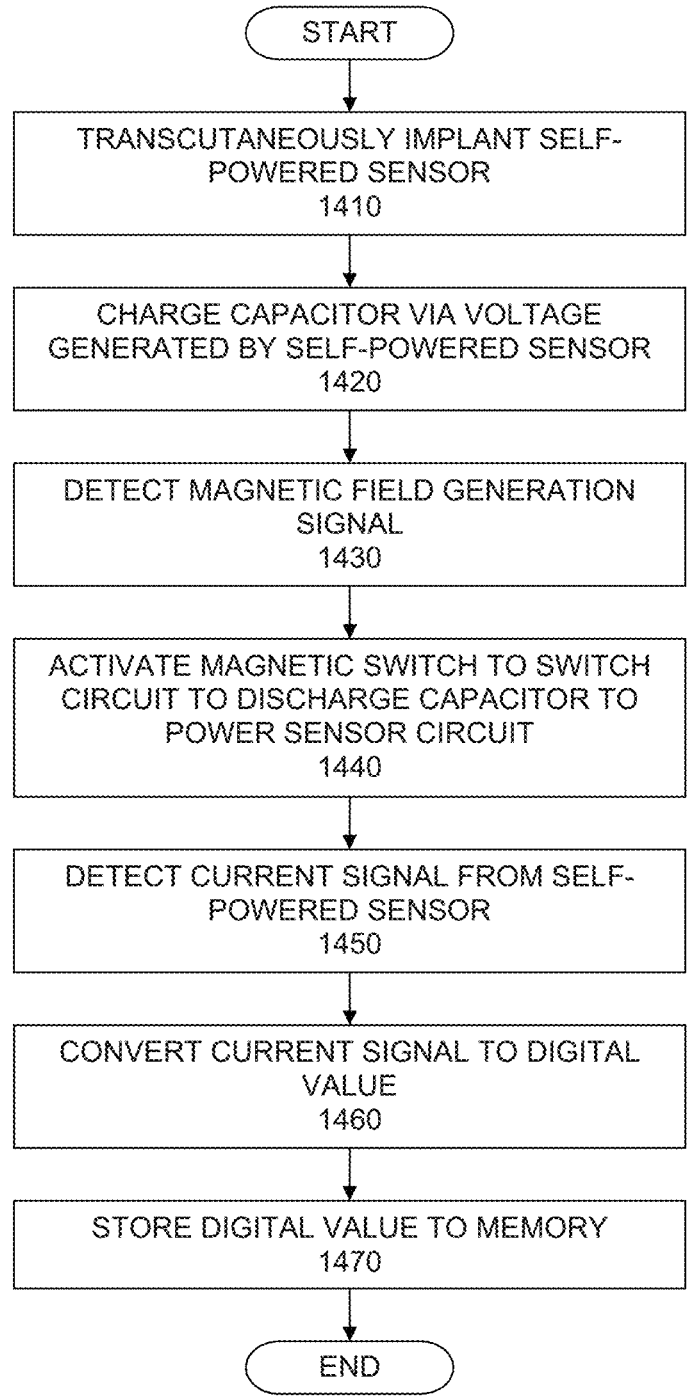
FIG. 14 is a flow chart illustrating a method of monitoring a level of an analyte of a user in accordance with embodiments of the present disclosure.

FIG. 14 is a flow chart illustrating analyte monitoring in certain embodiments of the present disclosure. As shown in FIG. 14, after transcutaneous positioning of a self-powered analyte sensor (1410), the oxidation reaction between the working and counter electrodes of the self-powered analyte sensor generates current signals. The generated current signals are used by the sensor electronics to charge a capacitor for storage of power for powering the sensor electronics (1420). Periodically, the sensor electronics detect a signal generated by a magnetic field generator corresponding to a command to measure a current analyte level (1430). Upon receipt of the magnetic field generated signal, the magnetic switch in the sensor electronics is activated, which switches the flow of power between the self-powered sensor and capacitor to discharge the capacitor to power the sensor electronics (1440). The reversed flow from the capacitor flows through a wire loop, which in turn generates a magnetic field signal indicative of a verification of connection of the magnetic switch. Upon activation of the magnetic switch, and subsequent activation of the sensor electronics, the current signal measured at the self-powered sensor representative of a current analyte level is detected by the sensor electronics (1450). The measured current signal of the self-powered sensor is converted to a digital value (1460) by the A/D converter of the sensor electronics. The digital value is then stored in memory (1470) for later retrieval or transmission to a display device.

In the manner described above, in accordance with embodiments of the present disclosure, solely using the signals generated by the oxidation reaction of the self-powered sensor, the generated signals provide sufficient power to drive the sensor electronics for processing signals related to the monitored analyte level, including storing, filtering, processing and for communication to a remote location. In this manner, in certain embodiments, sensor electronics coupled to the self-powered analyte sensor does not require a separate power source such as a battery to power the sensor electronics for processing signals related to the monitored analyte level including storing the generated and processed signals. In further embodiments, a remote device such as a display device is configured to generate a magnetic field which, when positioned in close proximity to the sensor electronics, latches a switch in the sensor electronics to drive the charge stored in the sensor electronics capacitor (generated from the self-powered sensor) to connect the remaining portions of the sensor electronics, effectively powering the sensor electronics solely from the charge stored in the capacitor that was generated by the self-powered sensor.

In a further embodiment, an on body sensor device including the self-powered sensor and sensor electronics is provided in a sealed housing and which does not include electronic components susceptible to sterilization processes for the sensor, and that would otherwise degrade or damage such electronic components. In this manner, in certain embodiments, a single enclosed housing including sensor electronics and the analyte sensor are provided which can be sterilized together using a single sterilization technique without damaging or degrading the components of the on body sensor device.

An analyte monitoring device in certain embodiments includes a self-powered analyte sensor having at least a portion in fluid contact with interstitial fluid under a skin surface, and sensor electronics operatively coupled to the self-powered analyte sensor, configured to receive signals generated by the self-powered analyte sensor, and to communicate data corresponding to analyte level monitored by the self-powered analyte sensor, the sensor electronics including: a buffering circuit operatively coupled to the self-powered analyte sensor for receiving the generated signals from the self-powered analyte sensor, and a radio frequency identification device (RFID) circuit operatively coupled to the buffering circuit and configured to communicate data corresponding to the generated signals associated with the monitored analyte level.

An analyte monitoring device in certain embodiments of the present disclosure includes a self-powered analyte sensor, and sensor electronics operatively coupled to the self-powered analyte sensor configured to receive signals generated by the self-powered analyte sensor and to communicate data corresponding to analyte level monitored by the self-powered analyte sensor, where the sensor electronics transitions from an inactive state to an active state when powered by a remote power source and upon receipt of a query signal from the remote power source, and in response to the query signal, communicates data corresponding to the generated signals associated with the monitored analyte level to the remote power source.

In certain embodiments, the self-powered analyte sensor is configured to continuously generate signals corresponding to monitored analyte level when in fluid contact with interstitial fluid.

In certain embodiments, the self-powered analyte sensor generates the signals corresponding to monitored analyte level when the sensor electronics are in the inactive state.

In certain embodiments, the sensor electronics are not operational when in the inactive state.

In certain embodiments, the sensor electronics include a buffering circuit operatively coupled to the self-powered analyte sensor for receiving the generated signals from the self-powered analyte sensor.

In certain embodiments, the sensor electronics includes a radio frequency identification device (RFID) circuit operatively coupled to the buffering circuit and configured to communicate data corresponding to the generated signals associated with the monitored analyte level.

In certain embodiments, the analyte monitoring device further includes a housing enclosing the self-powered sensor and the sensor electronics, wherein the housing is sealed to inhibit moisture from entering the housing.

In certain embodiments, the query signal includes an RFID signal.

In certain embodiments, the sensor electronics transition from the active state to the inactive state when the sensor electronics is not within the range of the remote power source.

In certain embodiments, the self-powered sensor is configured to generate the signals when in contact with the interstitial fluid and when the sensor electronics is in the inactive state.

In certain embodiments, the analyte monitoring device includes a housing enclosing the self-powered sensor and the sensor electronics, the housing including one or more mechanical components for physically detachably engaging with a remote device.

In certain embodiments, the remote device includes the remote power source.

In certain embodiments, the one or more mechanical components include one or more of a releasable latch, a releasable arm, or a releasable lock.

An analyte monitoring device, in certain embodiments, includes a self-powered analyte sensor having at least a portion in fluid contact with interstitial fluid under a skin surface, and sensor electronics operatively coupled to the self-powered analyte sensor configured to receive signals generated by the self-powered analyte sensor and to communicate data corresponding to analyte level monitored by the self-powered analyte sensor, the sensor electronics including: a buffering circuit operatively coupled to the self-powered analyte sensor for receiving the generated signals from the self-powered analyte sensor; and a radio frequency identification device (RFID) circuit operatively coupled to the buffering circuit and configured to communicate data corresponding to the generated signals associated with the monitored analyte level, where the sensor electronics transitions from an inactive state to an active state when powered by a remote power source and upon receipt of a query signal from the remote power source, and in response to the query signal, communicates data corresponding to the generated signals associated with the monitored analyte level to the remote power source.

In certain embodiments of the present disclosure, using the signals generated by the oxidation reaction of the self-powered sensor accumulated over time and stored in a capacitor device, sufficient charge is accumulated to drive the sensor electronics for processing signals related to the monitored analyte level, including storing, filtering, processing and communicating to a remote location. In this manner, sensor electronics coupled to the self-powered analyte sensor does not require a separate power source such as a battery to power the sensor electronics for processing signals related to the monitored analyte level including storing the generated and processed signals.

In some embodiments, a remote device such as a display device is configured to generate a magnetic field which, when positioned in close proximity to the sensor electronics, latches a switch in the sensor electronics to drive the charge stored in the sensor electronics capacitor device (generated from the self-powered sensor) to connect the remaining portions of the sensor electronics, effectively powering the sensor electronics solely from the charge stored in the capacitor that was generated by the self-powered sensor.

In a further embodiment, the self-powered sensor and sensor electronics are provided in a sealed housing and which does not include electronic components susceptible to sterilization processes for the sensor, and that would otherwise degrade or damage such electronic components. In this manner, in certain embodiments, a single enclosed housing including sensor electronics and the analyte sensor are provided which can be sterilized together using a single sterilization technique without damaging or degrading the components of the on body sensor device.

A method of monitoring analyte levels, in certain embodiments, includes transcutaneously positioning an analyte sensor in fluid contact with interstitial fluid under a skin surface, accumulating charge for a predetermined time period in a capacitor device in sensor electronics, the capacitor device in signal communication with the analyte sensor and receiving signals from the analyte sensor, detecting a magnetic field exceeding a threshold level, latching a switch provided in the sensor electronics to couple the capacitor device in the sensor electronics to sensor signal processing components when the detected magnetic field exceeds the threshold level, and connecting the capacitor device to the sensor signal processing components to provide power to the sensor signals processing components with the accumulated charge in the capacitor device.

A device for monitoring analyte level, in certain embodiments, includes an analyte sensor for transcutaneous positioning in fluid contact with interstitial fluid, sensor electronics including: sensor signal processing components, a capacitor device operatively coupled to the analyte sensor to accumulate charge for a predetermined time period, and a switch configured to latch, when a magnetic field exceeding a threshold level is detected, to couple the capacitor device to sensor signal processing components, where when the switch is latched, the capacitor device is configured to provide power to the sensor signals processing components with the accumulated charge in the capacitor device.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. A method of monitoring analyte levels, comprising:
   generating a current by an analyte sensor when in contact with interstitial fluid, the current corresponding to monitored analyte levels;
   receiving, by a capacitor device in sensor electronics, the current through a switch in the sensor electronics to accumulate charge in the capacitor device, wherein the switch is positioned between the analyte sensor and the capacitor device, wherein the switch has a first state and a second state, wherein the capacitor device receives the current generated by the analyte sensor when the switch is in the first state and wherein the capacitor device is unable to receive the current generated by the analyte sensor when the switch is in the second state;
   switching, by the switch, from the first state to the second state upon detecting a first magnetic field generated by a display device that exceeds a threshold level;
   discharging, by the capacitor device when the switch is in the second state, accumulated charge to power one or more sensor signal processing components in the sensor electronics, wherein a first component of the one or more sensor signal processing components comprises a wire loop configured to generate a magnetic pulse signal indicating that the switch is in the second state by using the accumulated charge discharged from the capacitor device.

2. The method of claim 1, wherein the analyte sensor is a self-powered analyte sensor, and wherein the current generated by the analyte sensor is proportional to an analyte concentration in the interstitial fluid.

3. The method of claim 1, further comprising:
   generating, by the display device, the first magnetic field; and
   determining, by the display device, that the switch is in the second state upon detecting the magnetic pulse signal.

4. The method of claim 1, wherein a resistor is positioned between the analyte sensor and the switch for limiting the current received by the capacitor device from the analyte sensor.

5. The method of claim 1, further comprising:
   determining one or more analyte values based on the generated current when the switch is in the second state, and storing the determined one or more analyte values when the switch is in the second state, thereby resulting in stored analyte values.

6. The method of claim 1, further comprising:
   communicating one or more signals corresponding to the monitored analyte levels when the switch is in the second state from the sensor electronics to the display device.

7. The method of claim 3, further comprising:
   displaying, by the display device, a number of times the switch has been switched to the second state based on the determination that the switch is in the second state upon detecting the magnetic pulse signal.

8. The method of claim 1, further comprising:
determining one or more analyte values based on the generated current when the switch is in the second state;
storing the determined one or more analyte values when the switch is in the second state, thereby resulting in stored analyte values; and
communicating one or more signals indicative of the stored analyte values when the switch is in the second state from the sensor electronics to the display device.

9. The method of claim 1, further comprising:
switching, by the switch, from the second state to the first state upon detecting that the first magnetic field is below the threshold level.

10. A device for monitoring analyte levels, comprising:
an analyte sensor configured to generate current when in contact with interstitial fluid, the current corresponding to monitored analyte levels; and
sensor electronics comprising:
a capacitor device, a switch positioned between the analyte sensor and the capacitor device, and one or more sensor signal processing components, wherein:
the capacitor device is configured to receive the current through the switch to accumulate charge, wherein the switch has a first state and a second state, wherein the capacitor device is operably coupled to the analyte sensor when the switch is in the first state such that the capacitor device is able to receive the current, and wherein the capacitor device is operably decoupled from the analyte sensor when the switch is in the second state such that the capacitor device is unable to receive the current;
the switch is configured to switch from the first state to the second state upon detecting a first magnetic field generated by a display device that exceeds a threshold level; and
the capacitor is configured to discharge, when the switch is in the second state, accumulated charge to power the one or more sensor signal processing components, wherein a first component of the one or more sensor signal processing components comprises a wire loop configured to generate a magnetic pulse signal indicating that the switch is in the second state by using the accumulated charge discharged from the capacitor device.

11. The device of claim 10, wherein the analyte sensor is a self-powered analyte sensor, and wherein the current that the analyte sensor is configured to generate is proportional to an analyte concentration in the interstitial fluid.

12. The device of claim 10, wherein the sensor electronics further comprise a resistor positioned between the analyte sensor and the switch for limiting current received by the capacitor device from the analyte sensor.

13. The device of claim 10, wherein the sensor electronics are configured to determine one or more analyte values based on the generated current when the switch is in the second state and comprises a data storage unit configured to store the determined one or more analyte values when the switch is in the second state, thereby resulting in stored analyte values.

14. The device of claim 10, wherein the sensor electronics are configured to determine one or more analyte values based on the generated current when the switch is in the second state, and further comprise:
a data storage unit configured to store the determined one or more analyte values when the switch is in the second state, thereby resulting in stored analyte values, and
a data communication unit configured to communicate one or more signals indicative of the stored analyte values when the switch is in the second state from the sensor electronics to the display device.

15. The device of claim 10, wherein the switch is configured to switch from the second state to the first state upon detecting that the first magnetic field is below the threshold level.

* * * * *